US009951376B2

(12) United States Patent
Heyduk et al.

(10) Patent No.: US 9,951,376 B2
(45) Date of Patent: Apr. 24, 2018

(54) METHODS FOR THE SELECTION OF APTAMERS

(71) Applicant: Saint Louis University, St. Louis, MO (US)

(72) Inventors: Tomasz Heyduk, Ballwin, MO (US); Ewa Heyduk, Ballwin, MO (US)

(73) Assignee: Saint Louis University, St. Louis, MO (US)

( * ) Notice: Subject to any disclaimer, the term of this patent is extended or adjusted under 35 U.S.C. 154(b) by 620 days.

(21) Appl. No.: 14/590,634

(22) Filed: Jan. 6, 2015

(65) Prior Publication Data
US 2015/0191779 A1  Jul. 9, 2015

Related U.S. Application Data

(62) Division of application No. 11/916,776, filed as application No. PCT/US2006/018845 on May 16, 2006, now Pat. No. 8,945,840.

(60) Provisional application No. 60/689,470, filed on Jun. 10, 2005.

(51) Int. Cl.
C12Q 1/00 (2006.01)
C12Q 1/68 (2018.01)
C12N 15/10 (2006.01)

(52) U.S. Cl.
CPC ........ C12Q 1/6811 (2013.01); C12N 15/1048 (2013.01); C12Q 1/6804 (2013.01)

(58) Field of Classification Search
CPC ............ C12Q 1/6811; C12Q 2525/205; C12N 2310/10
See application file for complete search history.

(56) References Cited

U.S. PATENT DOCUMENTS

| | | |
|---|---|---|
| 4,894,347 A | 1/1990 | Hillyard et al. |
| 5,270,163 A | 12/1993 | Gold |
| 5,475,096 A | 12/1995 | Gold |
| 5,476,766 A | 12/1995 | Gold |
| 5,543,293 A | 8/1996 | Gold |
| 5,567,588 A | 10/1996 | Gold |
| 5,582,981 A | 12/1996 | Toole |
| 5,637,459 A | 6/1997 | Burke |
| 5,641,629 A | 6/1997 | Pitner |
| 5,650,275 A | 7/1997 | Pitner |
| 5,660,985 A | 8/1997 | Pieken |
| 5,670,637 A | 9/1997 | Gold |
| 5,683,867 A | 11/1997 | Biesecker |
| 5,688,935 A | 11/1997 | Stephens |
| 5,696,249 A | 12/1997 | Gold |
| 5,705,337 A | 1/1998 | Gold |
| 5,712,375 A | 1/1998 | Jensen |
| 5,723,289 A | 3/1998 | Eaton |
| 5,723,592 A | 3/1998 | Eaton |
| 5,750,342 A | 5/1998 | Stephens |
| 5,756,291 A | 5/1998 | Griffin |
| 5,763,566 A | 6/1998 | Jensen |
| 5,763,595 A | 6/1998 | Gold |
| 5,773,598 A | 6/1998 | Burke |
| 5,789,157 A | 8/1998 | Jensen |
| 5,789,160 A | 8/1998 | Eaton |
| 5,817,785 A | 10/1998 | Gold |
| 5,840,867 A | 11/1998 | Toole |
| 5,843,653 A | 12/1998 | Gold |
| 5,853,984 A | 12/1998 | Davis |
| 5,858,660 A | 1/1999 | Eaton |
| 5,861,254 A | 1/1999 | Schneider |
| 5,864,026 A | 1/1999 | Jensen |
| 5,874,218 A | 2/1999 | Drolet |
| 5,958,691 A | 9/1999 | Pieken |
| 5,962,219 A | 10/1999 | Gold |
| 5,989,823 A | 11/1999 | Jayasena |
| 5,998,142 A | 12/1999 | Gold |
| 6,001,570 A | 12/1999 | Grossman |
| 6,001,577 A | 12/1999 | Gold |
| 6,011,020 A | 1/2000 | Gold |
| 6,013,443 A | 1/2000 | Heilig |
| 6,024,918 A | 2/2000 | Hendriks et al. |
| 6,030,776 A | 2/2000 | Eaton |
| 6,048,698 A | 4/2000 | Eaton |
| 6,083,696 A | 7/2000 | Biesecker |
| 6,110,900 A | 8/2000 | Gold |
| 6,114,120 A | 9/2000 | Jensen |
| 6,127,119 A | 10/2000 | Stephens |
| 6,147,204 A | 11/2000 | Gold |
| 6,177,555 B1 | 1/2001 | Jayasena |

(Continued)

FOREIGN PATENT DOCUMENTS

JP  2003-508729 A  3/2003
WO  9700446  1/1997

(Continued)

OTHER PUBLICATIONS

Bevan et al., "Sequencing of PCR-amplified DNA," PCR Methods and Applications, Genome Res., 1992, pp. 222-228, vol. 1.
Heyduk, "Practical biophysics: Sensors for rapid detection of biological targets utilizing target-induced oligonucleotide annealing," Biophysical Chemistry, 2010, pp. 91-95, vol. 151.
International Search Report and Written Opinion dated Jun. 28, 2011 from related International Patent Application No. PCT/US2011/024547, 10 pages.
Notice of Allowance and Fee (s) Due related to U.S. Appl. No. 11/916,776 dated Sep. 19, 2014 with 5 pages.
Notice of Allowance dated Aug. 5, 2014 from related U.S. Appl. No. 11/916,776, 7 pages.
Notice of Allowance dated Oct. 1, 2014 from related U.S. Appl. No. 13/728,226; 8 pages.

(Continued)

*Primary Examiner* — J. E. Angell
(74) *Attorney, Agent, or Firm* — Polsinelli PC

(57) ABSTRACT

The present invention generally relates to methods for selecting aptamers. More specifically, the invention provides methods for the selection of at least one aptamer for use in combination with another epitope binding agent such as another aptamer, an antibody, or a double stranded nucleic acid. The invention also encompasses methods for simultaneously selecting at least two aptamers that each recognize distinct epitopes on a target molecule.

7 Claims, 24 Drawing Sheets

(56) References Cited

U.S. PATENT DOCUMENTS

| | | |
|---|---|---|
| 6,207,388 B1 | 3/2001 | Grossman |
| 6,225,058 B1 | 5/2001 | Munishkin |
| 6,261,774 B1 | 7/2001 | Pagratis |
| 6,261,783 B1 | 7/2001 | Jayasena |
| 6,287,772 B1 | 9/2001 | Stefano |
| 6,291,184 B1 | 9/2001 | Gold |
| 6,300,074 B1 | 10/2001 | Gold |
| 6,329,145 B1 | 12/2001 | Janjic |
| 6,331,398 B1 | 12/2001 | Gold |
| 6,344,318 B1 | 2/2002 | Gold |
| 6,376,190 B1 | 4/2002 | Gold |
| 6,380,377 B1 | 4/2002 | Dattagupta |
| 6,391,593 B1 | 5/2002 | Weston |
| 6,399,302 B1 | 6/2002 | Lannigan |
| 6,423,493 B1 | 7/2002 | Gorenstein |
| 6,451,588 B1 | 9/2002 | Egholm |
| 6,465,188 B1 | 10/2002 | Gold |
| 6,506,887 B1 | 1/2003 | Smith |
| 6,511,809 B2 | 1/2003 | Baez |
| 6,544,746 B2 | 4/2003 | Heyduk |
| 6,566,495 B1 | 5/2003 | Fodor et al. |
| 6,593,091 B2 | 7/2003 | Keys |
| 6,613,526 B2 | 9/2003 | Heilig |
| 6,680,377 B1 | 1/2004 | Stanton |
| 6,716,583 B2 | 4/2004 | Gold |
| 6,730,482 B2 | 5/2004 | Gold |
| 6,815,164 B2 | 11/2004 | Kurn |
| 6,878,515 B1 | 4/2005 | Landegren |
| 6,916,613 B2 | 7/2005 | Munishkin |
| 7,125,660 B2 | 10/2006 | Stanton |
| 7,172,865 B2 | 2/2007 | Heyduk |
| 7,282,328 B2 | 10/2007 | Kong |
| 7,306,904 B2 | 12/2007 | Landegren |
| 7,419,835 B2 | 9/2008 | Torres |
| 7,435,542 B2 | 10/2008 | Shi |
| 7,576,192 B2 | 8/2009 | Heyduk |
| 7,795,009 B2 | 9/2010 | Heyduk |
| 7,811,809 B2 | 10/2010 | Heyduk |
| 7,939,313 B2 | 5/2011 | Heyduk et al. |
| 8,431,388 B2 | 4/2013 | Heyduk |
| 8,592,202 B2 | 11/2013 | Heyduk et al. |
| 8,945,840 B2 | 2/2015 | Heyduk et al. |
| 8,956,857 B2 | 2/2015 | Heyduk et al. |
| 8,993,245 B2 | 3/2015 | Heyduk et al. |
| 9,040,287 B2 | 5/2015 | Chang et al. |
| 9,618,505 B2 | 4/2017 | Heyduk |
| 9,671,403 B2 | 6/2017 | Heyduk |
| 2002/0022224 A1 | 2/2002 | Hornby |
| 2002/0037506 A1 | 3/2002 | Lin |
| 2002/0051986 A1 | 5/2002 | Baez et al. |
| 2002/0064779 A1 | 5/2002 | Landegren |
| 2003/0087239 A1 | 5/2003 | Stanton |
| 2003/0207271 A1 | 11/2003 | Holwitt |
| 2003/0224435 A1 | 12/2003 | Seiwert |
| 2003/0232383 A1 | 12/2003 | Daunert |
| 2003/0232388 A1 | 12/2003 | Kreimer et al. |
| 2004/0053310 A1 | 3/2004 | Shi |
| 2004/0058378 A1 | 4/2004 | Kage |
| 2004/0067501 A1 | 4/2004 | Kage |
| 2004/0180360 A1 | 9/2004 | Wilson |
| 2004/0219523 A1 | 11/2004 | Stanton |
| 2005/0009050 A1 | 1/2005 | Nadeau et al. |
| 2005/0069910 A1 | 3/2005 | Turner |
| 2005/0089890 A1 | 4/2005 | Cubicciotti |
| 2005/0089899 A1 | 4/2005 | Cubicciotti |
| 2005/0095627 A1 | 5/2005 | Kolman |
| 2005/0106594 A1 | 5/2005 | Ellington |
| 2005/0112710 A1 | 5/2005 | Torres et al. |
| 2005/0221408 A1 | 10/2005 | Nalefski et al. |
| 2006/0110739 A1 | 5/2006 | Heyduk et al. |
| 2007/0154899 A1 | 7/2007 | Coull et al. |
| 2007/0287197 A1 | 12/2007 | Harris et al. |
| 2008/0044826 A1 | 2/2008 | Heyduk |
| 2008/0044834 A1 | 2/2008 | Heyduk |
| 2008/0171322 A1 | 7/2008 | Heyduk |
| 2009/0202990 A1 | 8/2009 | Heyduk et al. |
| 2010/0021899 A1 | 1/2010 | Ikebukuro et al. |
| 2010/0297654 A1 | 11/2010 | Heyduk |
| 2011/0091893 A1 | 4/2011 | Heyduk et al. |
| 2012/0028242 A1 | 2/2012 | Heyduk et al. |
| 2013/0034846 A1 | 2/2013 | Chang et al. |
| 2014/0243208 A1 | 8/2014 | Chang et al. |
| 2014/0248710 A1 | 9/2014 | Heyduk et al. |
| 2015/0219668 A1 | 8/2015 | Heyduk et al. |
| 2015/0226739 A1 | 8/2015 | Heyduk |
| 2015/0253315 A1 | 9/2015 | Chang et al. |
| 2016/0077088 A1 | 3/2016 | Chang et al. |

FOREIGN PATENT DOCUMENTS

| | | |
|---|---|---|
| WO | 20070329 | 11/2000 |
| WO | 2003064657 | 8/2003 |
| WO | 2003064657 A | 8/2003 |
| WO | 2003078449 A2 | 9/2003 |
| WO | 05059509 A2 | 6/2005 |
| WO | 2006128138 A | 11/2006 |
| WO | 2006135527 A1 | 12/2006 |
| WO | 2007005649 A2 | 1/2007 |
| WO | 2008108873 A1 | 9/2008 |
| WO | 2010059820 A2 | 5/2010 |
| WO | 2011100561 A1 | 8/2011 |
| WO | 2013016280 A2 | 1/2013 |
| WO | 2016/040830 A1 | 3/2016 |

OTHER PUBLICATIONS

Notice of Allowance dated Nov. 18, 2014 from related U.S. Appl. No. 13/133,198; 8 pages.
Notice of Allowance dated Jan. 27, 2015 from related U.S. Appl. No. 13/578,718; 11 page.
Notice of Allowance dated Feb. 10, 2015 from related Canadian Patent Application No. 2,660,129; 1 page.
Office Action related to U.S. Appl. No. 11/916,776 dated Jun. 14, 2010 with 8 pages.
Office Action related to U.S. Appl. No. 11/916,776 dated Jun. 30, 2011 with 12 pages.
Office Action dated Jan. 8, 2015 from related European Patent Application No. 03703998.9, 2 pages.
Office Action dated May 30, 2012 from related European Patent Application No. 03703998.9, 3 pages.
Office Action from related Chinese Patent Application No. 201280038577.0, dated Jul. 7, 2015; 15 pages.
Office Action dated Nov. 3, 2014 from related Chinese Patent Application No. 201280038577.0; 11 pages.
Office Action dated Mar. 19, 2015 from related Canadian Patent Application No. 2,787,483; 4 pages.
Office Action dated Oct. 1, 2008 from related U.S. Appl. No. 11/609,628; 13 pages.
Office Action dated May 19, 2014 from related European Patent Application No. 11742872.2; 3 pages.
Office Action dated Apr. 2, 2015 from related European Patent Application No. 11742872.2; 4 pages.
Office Action from related U.S. Appl. No. 14/234,329, dated Aug. 7, 2015; 44 pages.
Final Office Action dated Nov. 5, 2014 from related U.S. Appl. No. 13/578,718; 25 pages.
Office Action dated Dec. 19, 2014, from related European Patent Application No. 13194822.6; 4 pages.
Supplemental Notice of Allowability dated Mar. 5, 2015 from related U.S. Appl. No. 13/578,718; 4 pages.
Stoltenburg et al., "SELEX—A (r)evolutionary method to generate high-affinity nucleic acid ligands", Biomolecular Engineering, 2007, pp. 381-403, vol. 24, No. 4.
Summons to Oral Proceedings dated Dec. 19, 2013 from related European Patent Application No. 04813618.8; 2 pages.
Supplementary European Search Report dated Nov. 25, 2014 from related European Patent Application No. 12817830.8; 11 pages.
Abravaya, "Detection of point mutations with a modified ligase chain reaction (Gap-LCR)," Nucleic Acids Research, 1995, pp. 675-682, vol. 23, No. 4, Oxford University Press.

(56) References Cited

OTHER PUBLICATIONS

Bock, "Selection of Single-Stranded DNA Molecules that bind and Inhibit Human Thrombin," Nature, 1992, pp. 564-566, vol. 355, No. 6360.
Boder et al., "Yeast surface display for screening combinatorial polypeptide libraries," National Biotech., 1997, pp. 553-557, vol. 15.
Burgstaller et al., "Synthetic Ribozymes and the First Deoxyribozyme," Angew. Chem. Int. Ed. Engli., 1995, pp. 1189-1192, vol. 34, No. 11.
"Chemical bond", http://en.wikipedia.org/wiki/Chemical_bon, printed Jun. 24, 2008, 11 pages.
Daniels, "Generation of RNA Aptamers to the G-Protein-Coupled Receptor for Neurotensin, NTS-1," Analytical Biochemistry, 2002, Elsevier Science, 2002, pp. 214-226, vol. 305.
Decision to Grant dated Sep. 5, 2013 related to European Patent Application No. 07873908.3, 2 pages.
Decision of Refusal dated Aug. 23, 2011 from related Japanese Patent Application No. 2006-543991, 3 pages with English Translation.
Decision on Oral Proceedings dated May 26, 2010 from related European Patent Application No. 04813618.8, 7 pages.
Decision to Grant dated Nov. 14, 2011 from related European Patent Application No. 06770407.2, 5 pages.
Ellington et al., "In vitro selection of RNA molecules that bind specific ligands," Nat., 1990, vol. 346, pp. 818-822.
Extended European Search Report, dated Dec. 22, 2009 for related European Patent Application No. 07873908.3, 6 pages.
European Supplementary Search Report dated Apr. 10, 2008 from related European Patent Application No. 04813618.8, 2 pages.
Extended European Search Report dated Jul. 9, 2010 from related European Patent Application No. 06770407.2, 4 pages.
European Search Report dated Nov. 16, 2009, from related Application No. EP 07873908, 2 pages.
Extended European Search Report dated Jan. 17, 2014, from related European Patent Application No. 13194822.6, 6 pages.
Extended European Search Report dated Aug. 23, 2013 from related European Patent Application No. 1174272.2, 6 pages.
Fredricksson, "Protein detection using proximity-dependent DNA ligation assays," Nature Biotechnology, 2002, Nature Publishing Group, vol. 20, pp. 473-477.
Fried et al., "Equilibria and kinetics of lac repressor-operator interactions by polyacrylamide gel electrophoresis," Nucl. Acid Res., Dec. 11, 1981, vol. 9, No. 23, pp. 6505-6525.
Francisco et al., "Production and fluorescence-activated cell sorting of *Escherichia coli* expressing a functional antibody fragment on the external surface." Proc. Natl. Acad. Sci., Nov. 15, 1993, pp. 10444-10448, vol. 90, No. 22.
Famulok et al., "Selection of Functional RNA and DNA Molecules from Randomized Sequences." Nucl. Acids and Mol. Biology, vol. 7.
Final Office Action dated Aug. 3, 2010 from related U.S. Appl. No. 11/836,339, 13 pages.
Famulok et al., "In Vitro Selection of Specific Ligand-binding Nucleic Acids," Angew Chem. Int. Ed. English, 1992, vol. 31, pp. 979-988.
Fang et al., "Synthetic DNA Aptamers to Detect Protein Molecular Variants in a High-Throughput Fluorescence Quenching Assay," ChemBioChem. 2003, pp. 829-834, vol. 4.
Georgiou et al., "Display of heterologous proteins on the surface of microorganisms: From the screening of combinatorial libraries to live recombinant vaccines," Nat., Biotech, Jan. 1997, vol. 15, pp. 29-34.
Gold et al., "Diversity of Oligonucleotide Functions," Ann. Rev. Biochem, 1995, vol. 64, pp. 763-797.
Hanes et al., "In vitro selection and evolution of functional proteins by using ribosome display," PNAS, May 1997, vol. 94, pp. 4937-4942.

Heyduk et al., "Molecular Pincers: Antibody-Based Homogeneous Protein Sensors," Anal. Chem., Jul. 1, 2008, vol. 80, No. 13, pp. 5152-5159.
Heyduk, "Nucleic Acid-Based Fluorescence Sensors for Detecting Proteins," American Chemical Society, Feb. 15, 2005, vol. 77, No. 4, pp. 1147-1156.
Heyduk et al., "Fluorescent homogenous immunosensors for detecting pathogenic bacteria," Anal. Biochem, Sep. 24, 2010, vol. 396, No. 2, pp. 298-303.
Heyduk et al., "Conformational Changes of DNA Induced by Binding of Chironomus High Mobility Group Protein 1a (cHMG1a)," Journal of Biology, 1997, vol. 272, No. 32, pp. 19763-19770.
Heyduk et al., "Homogeneous Fluorescence Assay for Cyclic AMP," Comb. Chem and High Throughput Screen, 2003, vol. 6, pp. 347-354.
Heyduk et al., "Thiol-reactive, Luminescent Europium Chelates: Luminscence Probes for Resonance Energy Transfer Distance Measurements in Biomolecules," Anal. Biochem., 1997, vol. 248, pp. 216-227.
Heyduk et al., "Molecular beacons for detecting DNA binding proteins, mechanism of action," Analyt. Biochem, 2003, vol. 316, pp. 1-10.
Heyduk et al., "Luminscense Energy Transfer with Lanthanide Chelates: Interpretation of Sensitized Acceptor Decay Amplitudes," Analyt. Biochem, 2001, vol. 289, No. 1, pp. 60-67.
Heyduk et al., "Molecular beacons for detecting DNA binding proteins," Nat. Biotech, 2002, vol. 20, pp. 171-176.
"HyTher-Hybridization Thermodynamics—Module 1", http://ozone2.chem.wayne.edu/cgi-bin/login/execs/HytherMI.cgi., printed on Mar. 5, 2009, 1 page.
Hosse et al., "A new generation of protein display scaffolds for molecular recognition," Protein Science, 2006, vol. 15, pp. 14-27.
Hamaguchi et al., "Aptamer Beacons for the Direct Detection of Proteins," Analyt. Biochem., 2001, vol. 294, pp. 126-131.
International Search Report and Written Opinion related to PCT/US07/75560 dated Aug. 25, 2008, 3 pages.
International Search Report and Written Opinion dated Jan. 11, 2013, related to PCT/US12/47840, 19 pages.
International Search Report and Written Opinion dated Sep. 24, 2007 from related PCT/US2004/041315, 6 pages.
International Search Report and Written Opinion dated Jan. 20, 2010 from related PCT/US2009/065142, 7 pages.
International Search Report and Written Opinion dated Aug. 3, 2007 related to PCT/US2006/018845, 4 pages.
Jayasena, "Aptamers: An Emerging Class of Molecules that Rival Antibodies in Diagnostics," Clin. J. Chem, 1999, vol. 45, No. 9, pp. 1628-1650.
Jeppesen et al., "Impact of Poloymer Tether Length on Multiple Ligand-Receptor Bond Formation," Science, Jul. 20, 2011, vol. 293, pp. 465-468.
Keefe et al., "Functional proteins from a random-sequence library," Nature, Apr. 5, 2001, vol. 410, pp. 715-718.
Klug et al., "All you wanted to know about SELEX (but were afraid to ask . . . )," Mol. Biol. Reg 1994, vol. 20, pp. 97-107.
Knoll et al., "Unimolecular Beacons for the Detection of DNA-Binding Proteins," Anal. Chem. 2004, vol. 76, No. 4, pp. 1156-1164.
Lipovsek et al., "In-vitro protein evolution by ribosome display and mRNA display," Journal Imm. Methods, 2004, vol. 290, pp. 51-67.
Order Rescheduling Oral Proceedings dated Jan. 28, 2014 from related European Patent Application No. 04813618.8, 1 page.
Oligonucleotide Modifications (TriLink Products) screen from http://www.trilinkbiotech.com/products/oligo/details_modifications.asp?Product_ID=133, printed Sep. 8, 2009, 1 page.
Ozawa et al., "Identification and Characterization of Peptides Binding to Newcastle Disease Virus by Phage Display," J. Vet. Med. Sci., 2005, vol. 67, No. 12, pp. 1237-1241.
Roberts et al., RNA-peptide Fusions for the in vitro selection of peptides and proteins, PNAS, 1997, vol. 94, No. 23, pp. 12297-12302.
Request for Postponement of Oral Proceedings dated Jan. 27, 2014 from related European Patent Application No. 04813618.8, 1 page.

(56) References Cited

OTHER PUBLICATIONS

Response to Communication Under Article 15(1) of the Rules of Procedure of the Board of Appeals dated Aug. 1, 2014 from related European Patent Application No. 04813618.8, 8 pages.
Rockett et al., "DNA arrays: technology, options and toxicological applications," Xenobiotica, 2000, vol. 30, No. 2, pp. 155-177.
Ratilainen et al., "Hybridization of Peptide Nucleic Acid," Biochemistry, 1998, vol. 37, pp. 12331-12342.
Result of Telephone Consultation with Examiner dated Apr. 13, 2010 from related European Patent Appication No. 04813618.8, 3 pages.
Sayer, "Structural characterization of a 2′F-RNA aptamer that binds a HIV-1 SU glycoprotein, gp120" Biochemical and Biophysical Research Communications, 2002, Academic Press, vol. 293, pp. 924-931.
Sequence alignment brochure SEQ ID No. 1 and 3, http://blast.ncbi.nim.nih.gov/Blast.cgi, printed Sep. 15, 2009, 1 page.
Sequence alignment brochure SEQ ID No. 2 and 3, http://blast.ncbi.nim.nih.gov/Blast.cgi, printed Sep. 13, 2009, 1 page.
Sequence alignment brochure SEQ ID No. 5 and 12, http://blast.ncbi.nim.nih.gov/Blast.cgi, printed Sep. 13, 2009, 1 page.
Sequence alignment brochure SEQ ID No. 7 and 12, http://blast.ncbi.nim.nih.gov/Blast.cgi, printed Sep. 15, 2009, 1 page.
Sequence alignment brochure SEQ ID No. 1 and 2, http://blast.ncbi.nim.nih.gov/Blast.cgi, printed Sep. 13, 2009, 1 page.
Selvin, et al., "Luminescence energy transfer using a terbium chelate: Improvements on fluorescence energy transfer," Proc. Natl. Acad. Si., USA 1994, vol. 91, pp. 10024-10028.
Selvin et al., "Luminescence Resonance Energy Transfer," J. Am. Chem. Soc. 1994, vol. 116, pp. 6029-6030.
Santalucia, "A unified view of polymer, dumbbell and oligonucleotide DNA nearest-neighbor thermodynamics." PNAS, 1998, vol. 95, pp. 1460-1465.
Supplementary European Search Report dated Jun. 11, 2010 from elated EP Application No. EP 06770407, 1 page.
Sen, "On the Stability of Peptide Nucleic Acid Duplexes in the Presence of Organic Solvents," Nucleic Acids Research, vol. 35, No. 10, pp. 3367-3374.
Santalucia, "Improved Nearest-Neighbor Parameters for Predicting DNA Duplex Stability," Biochemistry, 1996, pp. 3555-3562.
Statement of Grounds for Appeal dated Oct. 15, 2010 from related European Patent Application No. 04813618.8, 22 pages.
Tasset, "Oligonucleotide Inhibitors of Human Thrombin That Bind Distinct Epitopes," Journal of Molecular Biology, 1997, vol. 272, No. 5, pp. 688-698.
Tanaka, "Specificity of Hybridization Between DNA Sequences based on Free Energy", DNA Computing, 2006, 371-379, Springer-Verlag, Berlin.
Telephone Consultation Records faxed May 6, 2010 regarding telephone interviews held on Apr. 27 and May 3, 2010 for related European Patent Application No. 04813618.8, 5 pages.
Tuerk et al., "Systematic Evolution of Ligands by Exponential Enrichment: RNA Ligands to Bacteriophage T4 DNA Polymerase," Sci. 1990, vol. 249, No. 4968, pp. 505-510.
Upitma FT-UP17412 SMCC, sSMCC Heterobifunctional cross-linkers brochure, 3 pages.
Uptima FT-UP79042 SPDP, lc-SPDP, Sufo-lc-SPDP Heterobifunctional cross-linkers brochure, not dated (date provided by Examiner was Sep. 15, 2009), 3 pages, Office Action dated Sep. 30, 2009, in related U.S. Appl. No. 11/836,333.
Uptima FT-UP17412 SMCC sSMCC Heterobifunctional cross-linkers brochure, undated (no date was provided by Examiner), 3 pages, Office Action dated Jul. 2, 2008 in related U.S. Appl. No. 10/539,107.
Wilson et al., "In Vitro Selection of Functional Nucleic Acids," Ann. Rev. Biochem., 1999, vol. 68, pp. 611-647.
Written Submission dated Apr. 22, 2010 from related European Patent Application No. 04813618.8, 21 pages.
Written Submission dated Apr. 30, 2010 fromr elated European Patent Application No. 04813618.8, 37 pages.
Written Submission dated Apr. 6, 2010 from related European Patent Application No. 04813618.8, 16 pages.
Xu et al., "Anti-peptide aptamers recognize amino acid sequence and bind a protein epitope," Proc. Natl. Acad. Sci. USA, 1996, vol. 93, pp. 7475-7480.
Yamamoto et al., "Molecular beacon aptamer fluoresces in the presence of TAT Protein of hiv-1," Genes Cells, 2000, vol. 5, pp. 389-396.
Zhang et al., "A Simple Statistical Parameter for Use in Evaluation and Validation of High Throughput Screening Assays," J. Biomol. Screenings, 1999, No. 4, No. 2, pp. 67-73.
Zalipski, "Chemistry of polyethylene glycol conjugates with biologically active molecules," Advanced Drug Delivery Reviews, Elsevier Science B.V., 1995, vol. 16, pp. 157-182.
Lass-Napiorkowska et al., "Detection Methodology Based on Target Molecule-Induced Sequence-Specific Binding to Single-Stranded Oligonucleotide," Anal. Chem., 2012, vol. 84, pp. 3382-3389.
Li et al., "Molecular Aptamer Beacons for Real-Time Protein Recognition," Biochem. and Biophys. Res. Commun., 2002, vol. 292, No. 1, pp. 31-40.
Mathis, "Probing Molecular Interactions with Homogeneous Techniques Based on Rare Earth Cryptrates and Fluorescence Energy Transfer," Clinic. Chem. 1995, vol. 41, No. 9, pp. 1391-1397.
Matlock et al. "Sequence Determinants for the Recognition of the Fork Junction DNA Containing the −10 Region of Promoter DNA by *E. Coli* RNA Polymerase," Biochem., 2000, vol. 39, No. 40, pp. 12274-12283.
Mills et al., "Flexibility of Single-Stranded DNA: Use of Gapped Duplex Helices to Determine the Persistence Lengths of Poly(dT) and Poly (dA)," J. Mol. Biol., 1999, vol. 285, pp. 245-257.
Minutes of Oral Proceedings dated May 20, 2010 from related European Patent Application No. 04813618.8, 5 pages.
Notice of Allowance dated Feb. 29, 2012 from related Chinese Patent Application No. 200480036874.7, 3 pages.
Notice of Allowance and Interview Summary dated Dec. 20, 2012 for related U.S. Appl. No. 12/830,958, 16 pages.
Notice of Allowance dated Jul. 24, 2013 from related U.S. Appl. No. 12/961,135, 27 pages.
Notice of Allowance dated Jun. 16, 2014 from related U.S. Appl. No. 13/728,226, 21 pages.
Notice of Allowance dated Aug. 19, 2014 from related Canadian Patent Application No. 2,611,198, 1 page.
Notice of Allowance dated Aug. 28, 2014 from related U.S. Appl. No. 13/133,198, 13 pages.
Office Action dated Sep. 14, 2009 from related U.S. Appl. No. 11/836,339, 22 pages.
Office Action dated Sep. 30, 2009 from related U.S. Appl. No. 11/836,333, 33 pages.
Office Action dated Mar. 12, 2009 from related U.S. Appl. No. 10/539,107, 24 pages.
Office Action dated Jul. 2, 2008 from related U.S. Appl. No. 10/539,107, 21 pages.
Office Action dated Dec. 18, 2009 from related U.S. Appl. No. 10/539,107, 21 pages.
Office Action dated May 8, 2012 from related U.S. Appl. No. 12/830,958, 21 pages.
Office Action dated Feb. 23, 2010 from related Japanese Patent Appication No. 2006-543991, 3 pages with 3 pages of English Translation.
Office Action dated Nov. 5, 2012 for related U.S. Appl. No. 13/133,198, 12 pages.
Office Action dated Nov. 20, 2012 for related Canadian Patent Application No. 2,611,198, 3 pages.
Office Action dated Apr. 4, 2011 from related European Patent Application No. 06770407.2, 3 pages.
Office Action dated Aug. 9, 2010 from related Chinese Patent Application No. 200480036874.7, with 14 pages of English translation.
Office Action dated Dec. 1, 2011 from related U.S. Appl. No. 12/961,135, 23 pages.
Office Action dated Dec. 18, 2008 from related European Patent Application No. 04813618.8, 3 pages.

(56) References Cited

OTHER PUBLICATIONS

Office Action dated Feb. 3, 2011 from related Canadian Patent Application No. 2,545,006, 5 pages.
Office Action dated Jan. 4, 2012 from related European Patent Application No. 07873908.3, 3 pages.
Office Action dated Jan. 9, 2011 from related Chinese Patent Application No. 200480036874.7, with 7 pages of English translation.
Office Action dated Jul. 1, 2008 from related European Patent Application No. 04813618.8, 3 pages.
Office Action dated Jun. 17, 2011 from related U.S. Appl. No. 12/961,135, 36 pages.
Office Action dated Nov. 24, 2010 from related Japanese Patent Application No. 2006-543991, 2 pages with English translation.
Office Action dated Oct. 10, 2011 from related Chinese Patent Application No. 200780037379.1, 7 pages with English translation.
Office Action dated Oct. 26, 2010 from related European Patent Application No. 07873908.3, 5 pages.
Office Action dated Sep. 8, 2011 from related Chinese Patent Application No. 200480036874.7, 5 pages with English translation.
Office Action dated Jul. 10, 2012 for related Chinese patent Application No. 200780037379.1, 8 pages with 1 page English translation.
Office Action dated May 27, 2013 from related Chinese Patent Application No. 200980146720.6, with 18 pages of English translation.
Office Action dated Dec. 10, 2013 from related Chinese Patent Application No. 200980146720.6, 34 pages including English translation.
Office Action dated May 20, 2014 from related Chinese Patent Application No. 200980146720.6, 25 pages including English translation.
Office Action dated Jul. 29, 2014 from related Japanese Patent Application No. 2011-284014, 1 page English translation only.
Office Action dated Oct. 8, 2013 from related Japanese Patent Application No. 2011-284014, 2 pages of English translation only.
Office Action dated Aug. 21, 2013 from related Canadian Patent Application No. 2,660,129, 3 pages.
Office Action dated Feb. 19, 2014 from related Canadian Patent Application No. 2,787,483, 3 pages.
Office Action dated Aug. 30, 2013 from related Canadian Patent Application No. 2,611,198, 2 pages.
Office Action dated Dec. 27, 2013 from related Canadian Patent Application No. 2,744,003, 2 pages.
Office Action dated Mar. 26, 2013 from related Canadian Patent Application No. 2,744,003, 3 pages.
Office Action dated Nov. 27, 2013 from related Indian Patent Application No. 1337/CHENP/2009, 4 pages.
Office Action with Examiner Initiated Interview Summary dated Jun. 27, 2013 from related U.S. Appl. No. 13/133,198, 14 pages.
Office Action dated Sep. 13, 2013 from related U.S. Appl. No. 13/578,718, 24 pages.
Office Action with Interview Summary dated Feb. 21, 2014 from related U.S. Appl. No. 13/578,718, 32 pages.
Office Action dated Jan. 10, 2014 from related U.S. Appl. No. 13/728,226, 30 pages.
Darmanis et al., "Self-assembly of proximity probes for flexible and modular proximity ligation assays", BioTechniques, 2007, pp. 443-450, vol. 43, No. 4.
International Search Report and Written Opinion from related International Patent Application No. Pct/US2015/049733, dated Jan. 29, 2016; 15 pgs.
Office Action from related U.S. Appl. No. 14/234,329, dated Apr. 1, 2016; 10 pgs.
Office Action from related U.S. Appl. No. 14/623,348, dated Jun. 17, 2016; 21 pgs.
Office Action from related Chinese Patent Application No. 200480036874.7, dated Jan. 19, 2011; 12 pages (with English translation).
Office Action from related Chinese Patent Application No. 200480036874.7, dated Jun. 23, 2011; 9 pages (with English translation).
Office Action from related U.S. Appl. No. 11/836,339, dated Mar. 8, 2010; 14 pages.
Office Action dated May 30, 2016 from related Canadian Patent Application No. 2,787,483; 3 pages.
Office Action from related U.S. Appl. No. 14/234,329, dated Nov. 16, 2016; 13 pages.
Notice of Allowance dated Nov. 25, 2016 from related U.S. Appl. No. 14/623,348; 14 pages.
Office Action from related U.S. Appl. No. 14/673,336, dated Aug. 8, 2016; 60 pages.
Notice of Allowance dated Jan. 31, 2017 from related U.S. Appl. No. 14/673,336; 10 pages.
Office Action from related U.S. Appl. No. 14/719,867, dated Nov. 8, 2016; 68 pages.
Notice of Allowance dated Apr. 24, 2017 from related U.S. Appl. No. 14/719,867; 10 pages.

| clone | sequence | |
|---|---|---|
| clone1 | ----------GGCGGT-ATGGGCATAGCGTAATGGG-AGGTTGGT------------------------------- | 33 |
| clone9 | ----------GGCGGT-ATGGGTATAGCGTAATGGG-AGGTTGGT------------------------------- | 33 |
| clone7 | ----------GGCGGT-ATGGGCATAGCGTAATGGG-AGGTCTGC------------------------------- | 33 |
| clone12 | ---------GCGGNGATAGGTCGCGTAAGTTGGGTGGGTAGGGTGG------------------------------ | 33 |
| clone2 | ----------GGATGCGTAATGGTTAGGGTGGGTAGGGTAGGGTATCC---------------------------- | 33 |
| clone3 | ----------GGATGCGTAATGGTTAGGGTGGGTAGGGTAGGGTATCC---------------------------- | 33 |
| clone4 | ----------GGATGCGTAATGGTTAGGGTGGGTAGGGTAGGGTATCC---------------------------- | 33 |
| clone8 | ----------GGATGCGTAATGGTTAGGGTGGGTAGGGTAGGGTATCC---------------------------- | 33 |
| clone23 | ----------GCATACGTAATGTCCGGTTGGGTTGGGCGGGTATGT------------------------------ | 33 |
| clone22 | ----------GGAGACGTAATGGGTTGGTTGGGTGGGAAGNGATCC------------------------------ | 33 |
| clone11 | CAGCAGGAACGGAACGGTTAGGGTGGGTAGG--------------------------------------------- | 33 |
| clone32 | ---------GCAGTAGGTACTATATTGGCTAGGGTGGTCTGC---------------------------------- | 33 |
| clone33 | ---------GCAGTAGGTACTATATTGGCTAGGGTGGTCTGC---------------------------------- | 33 |
| clone29 | ---------GCAGTAGGTACTATATTGGCTAGGGTGGTCTGC---------------------------------- | 33 |
| clone31 | ---------GCAGTAGGTACTATATTGGCTAGGGTGGTCTGC---------------------------------- | 33 |
| clone5 | ---------GCAGTAGGTACTATATTGGCTAGGGTGGTCTGC---------------------------------- | 33 |
| clone6 | ---------GCAGTAGGTACTATATTGGCTAGGGTGGTCTGC---------------------------------- | 33 |
| clone35 | ---------GCAGTAGGTACTATGTCGGGTCGGGTGGTCTGC---------------------------------- | 33 |
| clone10 | ---------GGGGGTACTAGGTATTAA--TGGGTAGGGTGGTGT-------------------------------- | 33 |
| clone34 | ---------GGGGGTGCTAGGTATTAA--AGGGTAGGGTGGTGT-------------------------------- | 33 |
| clone20 | ---------GGGGGTACTAGGTATCAA--TGGGTAGGGTGGTGT-------------------------------- | 33 |
| clone21 | ---------GGGGGTACTAGGTATCAA--TGGGTAGGGTGGTGT-------------------------------- | 33 |
| clone24 | ---------GGGGGTACTAGGTATCAA--TGGGTAGGGTGGTGT-------------------------------- | 33 |
| clone26 | ---------GGGGGTACTAGGTATCAA--TGGGTAGGGTGGTGT-------------------------------- | 33 |
| clone13 | ---------------------------CAGGATGGTGGTAGGGTGGTCAGCGAAGCAGTAGG-------------- | 33 |
| clone15 | ---------------------------CAGGATGGTGGTAGGGTGGTCAGCGAAGCAGTAGG-------------- | 33 |
| clone16 | ---------------------------CAGGATGGTGGTAGGGTGGTCAGCGAAGCAGTAGG-------------- | 33 |
| clone19 | ---------------------------CAGGATGGTGGTAGGGTGGTCAGCGAAGCAGTAGG-------------- | 33 |
| clone25 | ----------GAGGGACTTAGGATAGGGTGGTAGGGTGGTAGGCCC------------------------------ | 33 |
| clone17 | ----------GGCGAGAGCAGCGTGAACTGTAGGGTGGGTAGGGTG------------------------------ | 33 |
| clone14 | ----------CAACGGTTGGGTGGCATAGT--AATGCTGGATTGGGCAGCT------------------------- | 33 |
| clone27 | ----------GGTCGGGGAGCAGTAC--A-CGCTGGAATGGGTCACT----------------------------- | 33 |
| clone28 | ----------GGGTAGGAGCAGTAC----GAGGACGGAATGGGC-ACT---------------------------- | 33 |
| clone30 | ----------GGGTAGGTGACAGG----GAGGACGGAATGGGC-ACT---------------------------- | 33 |
| clone18 | ---------CAGGGTCAGGGCTAGATGATGCGATTAACCATG--------------------------------- | 33 |
| ruler | 1.........10........20........30........40........50.. | |

```
clone1-1   ------GGGTAGGGTGGTGGTTGTAATAGGG----ATTGCGAT-     30
clone1-2   ------GGGTAGGGTGGTGGTTGTAATAGGG----ATTGCGAT-     30
clone1-4   ------GGGTAGGGTGGTGGTTGTAATAGGG----ATTGCGAT-     30
clone1-5   ------GGGTAGGGTGGTGGTTGTAATAGGG----ATTGCGAT-     30
clone1-9   ------GGGTAGGGTGGTGGTTGTAATAGGG----ATTGCGAT-     30
clone2-4   ------GGTAGGGTGGTGGTTAAAATAGGGAATGGCAG------     30
clone2-7   ------GGTAGGGTGGTGGTTAAAATAGGGAATGGCAG------     30
clone2-10  ------GGTAGGGTGGTGGTTAAAATAGGGAATGGCAG------     30
clone2-8   ------TAGGATGGGTAGGGTGGTCCCAGAATGGC---------     30
clone2-9   ------TAGGATGGGTAGGGTGGCCCCAGAATGGC---------     30
clone2-12  ------TACGATCGGTAGGGTGGTCCCAGAATGGC---------     30
clone2-14  ------TAGGATGGGTAGGGTGGTCCCAGAATGGC---------     30
clone1-8   ----ACGCGTAGGGATGGGTAGGGTGGTCGCGTTA---------     30
clone2-2   ------TAGGGTGGGTAGGGTGGTCAACTATGGGGG--------     30
clone1-7   ------AATGGGGAGGTTGGGGTGCGGGAGAGTGGT--------     30
clone2-5   ------CACAAGAAGGGCGAGCGCTGAGCATAGTGC--------     30
clone2-13  ------GGAGATGCAGGTACTGAGTAGGAGTGTGC---------     30
clone2-3   ------GGGTGGCTGCTCAAGGAG-ATAGTACGATGC-------     30
clone2-11  ---------GATG--TGGCCCAGAAGCATAACACGACGTAC--     30
clone2-1   ------AAGGCCGCCATCTGGGTCCGACGAGTACCA--------     30
clone1-10  ------GGGCGAAGGTACGAAGACGGATGCACGTGC--------     30
clone1-6   ------GGTGTGGGTGG-TTATTGGTGTAGAGCGGGT-------     30
clone1-3   ------GGCACAACCCGATATGGCTATGAATCTGCC--------     30
clone2-6   ------CCAACGACACATAGGGTACACGCCGCCTCC--------     30
ruler    1.........10........20........30.......40
```

Figure 8
C

| clone | sequence | |
|---|---|---|
| clone1 | AATCAAGGGCTGGTGTTAAAGGTGATCGACTAG------------------------- | 33 |
| clone23 | -------GAGGATAAAAGCCATCAACTAGAATGCCATGG------------------- | 33 |
| clone3 | ------------AAAGCCATCACCTAGAGTTGCCGCCGATACTTG------------- | 33 |
| clone17 | ------------ACAAGCCATCACGT-GAATGCCGACCGGTACTGT------------ | 33 |
| clone15 | -------------CAGGCATCCCAAGAAGTGTCAGCCGTTTCGTGG------------ | 33 |
| clone7 | ---------------AGGGAAAGCCATCACCT--AGACACATACAGCATG-------- | 33 |
| clone20 | ---------------AACGGGAAAGCCATCACC---ATATTTAT-CGTCCTG------ | 33 |
| clone5 | --------------CGAAAGGAGCCATCAACC-TTGAAACGCCCGTCC---------- | 33 |
| clone10 | ------------ACAGACGCCCTAGTAAACAATAAC-CGATGGCC------------- | 33 |
| clone13 | ------------GCAATATAGCACTAAGCCTTAACTCCATGGTGG------------- | 33 |
| clone2 | -----------AAGGGAGCCATCCATCAGGAGGTCGCTTCGCT--------------- | 33 |
| clone6 | -------------CAGACGGGAGCCATCGACATAGAGGTGATTGCC------------ | 33 |
| clone9 | -------------CCAACAGACGGTAGCACATAACACTAGTACTCTGG---------- | 33 |
| clone16 | -------------CAACAGGAG--AGCCCGACAC-ACAGATCTGGCCCC--------- | 33 |
| clone21 | -------------ACGGGCGCAAACAAGATGTACAAAAGCATGGTG------------ | 33 |
| clone4 | ------------GGGGATGTGCGAAACTGGTGACTATGCGG-GTGC------------ | 33 |
| clone22 | ------------AGCGGGATAGGGAACTATCGGACAATCGTCGTG------------- | 33 |
| clone8 | -------------ATAAGAAGCCA-TCATAGGGACCTAGCTAGCCCC----------- | 33 |
| clone14 | ------------GCAAGGAAACAAGCCATCAAGCCATCACGACCTAG----------- | 33 |
| clone18 | -------------ACCGACAAACAAGTCAATACGGGACACGATCCT------------ | 33 |
| clone12 | ------------ATGGGCAACGCGGAGACCTGTCGGTACTGCCT-------------- | 33 |
| clone19 | -------------CAGTGGGTCGGGTCACAGCCATGAGTGTTGCTG------------ | 33 |
| clone11 | -------------ATAGCTACTCGCCAAGGGTGACTTTCTGCTATTG----------- | 33 |
| ruler | 1........10........20........30........40........50.. | |

SEQUENCE LISTING

<160> NUMBER OF SEQ ID NOS: 96

<210> SEQ ID NO 1
<211> LENGTH: 69
<212> TYPE: DNA
<213> ORGANISM: Artificial
<220> FEATURE:
<223> OTHER INFORMATION: BASE ON MAMMALIAN
<220> FEATURE:
<221> NAME/KEY: misc_feature
<222> LOCATION: (19)..(51)
<223> OTHER INFORMATION: n is a, c, g, t, or u

<400> SEQUENCE: 1
ctgtcgttag tgaaggtnn nnnnnnnnn nnnnnnnnn nnnnnnnnn naacgccata      60 tcacagacg                                                          69

<210> SEQ ID NO 2
<211> LENGTH: 20

```
<212> TYPE: DNA
<213> ORGANISM: ARTIFICIAL
<220> FEATURE:
<223> OTHER INFORMATION: BASED ON MAMMALIAN
<220> FEATURE:
<221> NAME/KEY: misc_feature
<222> LOCATION: (15)..(16)
<223> OTHER INFORMATION: (spacer 18)x2 (18-atom hexaethyleneglycol
      chain)

<400> SEQUENCE: 2
ggttggtgtg gttgggacag                                              20

<210> SEQ ID NO 3
<211> LENGTH: 22
<212> TYPE: DNA
<213> ORGANISM: Artificial
<220> FEATURE:
<223> OTHER INFORMATION: BASED ON MAMMALIAN
<220> FEATURE:
<221> NAME/KEY: MISC_FEATURE
<222> LOCATION: (15)..(16)
<223> OTHER INFORMATION: (spacer 18)x5 (18-atom hexaethyleneglycol
      chain)

<400> SEQUENCE: 3
ggttggtgtg gttggacgac ag                                           22

<210> SEQ ID NO 4
<211> LENGTH: 23
<212> TYPE: DNA
<213> ORGANISM: Artificial
<220> FEATURE:
<223> OTHER INFORMATION: BASED ON MAMMALIAN
<220> FEATURE:
<221> NAME/KEY: misc_feature
<222> LOCATION: (15)..(16)
<223> OTHER INFORMATION: (spacer 18)x5 (18-atom hexaethyleneglycol
      chain)

<400> SEQUENCE: 4
ggttggtgtg gttggaacga cag                                          23

<210> SEQ ID NO 5
<211> LENGTH: 77
<212> TYPE: DNA
<213> ORGANISM: Artificial
<220> FEATURE:
<223> OTHER INFORMATION: BASED ON MAMMALIAN
<220> FEATURE:
<221> NAME/KEY: misc_feature
<222> LOCATION: (8)..(9)
<223> OTHER INFORMATION: (spacer 18)x5 (18-atom hexaethyleneglycol
      chain)
<220> FEATURE:
<221> NAME/KEY: misc_feature
<222> LOCATION: (27)..(59)
<223> OTHER INFORMATION: n is a, c, g, t, or u

<400> SEQUENCE: 5
ctgtcgtttt gagtcagcgt cgagcannnn nnnnnnnnnn nnnnnnnnnn nnnnnnnnnt   60
tcactgtgct gcggcta                                                 77

<210> SEQ ID NO 6
<211> LENGTH: 23
<212> TYPE: DNA
<213> ORGANISM: Artificial
<220> FEATURE:
<223> OTHER INFORMATION: BASED ON MAMMALIAN
<220> FEATURE:
```

```
<221> NAME/KEY: misc_feature
<222> LOCATION: (15)..(16)
<223> OTHER INFORMATION: (spacer 18)x5 (18-atom hexaethyleneglycol
      chain)
<220> FEATURE:
<221> NAME/KEY: modified_base
<222> LOCATION: (16)..(16)
<223> OTHER INFORMATION: C6 amino-dT

<400> SEQUENCE: 6
ggttggtgtg gttggtcgca tct                                              23

<210> SEQ ID NO 7
<211> LENGTH: 50
<212> TYPE: DNA
<213> ORGANISM: Artificial
<220> FEATURE:
<223> OTHER INFORMATION: BASED ON MAMMALIAN
<220> FEATURE:
<221> NAME/KEY: misc_feature
<222> LOCATION: (1)..(1)
<223> OTHER INFORMATION: 5'fluorescein
<220> FEATURE:
<221> NAME/KEY: misc_feature
<222> LOCATION: (7)..(8)
<223> OTHER INFORMATION: (spacer 18)x5 (18-atom hexaethyleneglycol
      chain)

<400> SEQUENCE: 7
agatgcgagg ttgggggtac taggtatcaa tgggtagggt ggtgtaacgc                 50

<210> SEQ ID NO 8
<211> LENGTH: 60
<212> TYPE: DNA
<213> ORGANISM: Artificial
<220> FEATURE:
<223> OTHER INFORMATION: BASED ON MAMMALIAN
<220> FEATURE:
<221> NAME/KEY: misc_feature
<222> LOCATION: (1)..(1)
<223> OTHER INFORMATION: 5'fluorescein
<220> FEATURE:
<221> NAME/KEY: misc_feature
<222> LOCATION: (7)..(8)
<223> OTHER INFORMATION: (spacer 18)x5 (18-atom hexaethyleneglycol
      chain)

<400> SEQUENCE: 8
agatgcgagt gaaggttggg ggtactaggt atcaatgggt agggtggtgt aacgccatat      60

<210> SEQ ID NO 9
<211> LENGTH: 36
<212> TYPE: DNA
<213> ORGANISM: Artificial
<220> FEATURE:
<223> OTHER INFORMATION: BASED ON MAMMALIAN
<220> FEATURE:
<221> NAME/KEY: misc_feature
<222> LOCATION: (1)..(1)
<223> OTHER INFORMATION: 5'fluorescein
<220> FEATURE:
<221> NAME/KEY: misc_feature
<222> LOCATION: (7)..(8)
<223> OTHER INFORMATION: (spacer 18)x5 (18-atom hexaethyleneglycol
      chain)

<400> SEQUENCE: 9
agatgcgagt ccgtggtagg gcaggttggg gtgact                                36

<210> SEQ ID NO 10
<211> LENGTH: 66
```

-continued

```
<212> TYPE: DNA
<213> ORGANISM: Artificial
<220> FEATURE:
<223> OTHER INFORMATION: BASED ON MAMMALIAN
<220> FEATURE:
<221> NAME/KEY: misc_feature
<222> LOCATION: (19)..(48)
<223> OTHER INFORMATION: n is a, c, g, t, or u

<400> SEQUENCE: 10
cacctgatcg ctcctcgtnn nnnnnnnnnn nnnnnnnnnn nnnnnnnnca ggatgcacag    60
gcacaa                                                               66

<210> SEQ ID NO 11
<211> LENGTH: 66
<212> TYPE: DNA
<213> ORGANISM: Artificial
<220> FEATURE:
<223> OTHER INFORMATION: BASED ON MAMMALIAN
<220> FEATURE:
<221> NAME/KEY: misc_feature
<222> LOCATION: (19)..(48)
<223> OTHER INFORMATION: n is a, c, g, t, or u

<400> SEQUENCE: 11
agccgccatt ccatagtgnn nnnnnnnnnn nnnnnnnnnn nnnnnnnnca ggatgccgat    60
caggtg                                                               66

<210> SEQ ID NO 12
<211> LENGTH: 69
<212> TYPE: DNA
<213> ORGANISM: Artificial
<220> FEATURE:
<223> OTHER INFORMATION: BASED ON MAMMALIAN
<220> FEATURE:
<221> NAME/KEY: misc_feature
<222> LOCATION: (19)..(51)
<223> OTHER INFORMATION: n is a, c, g, t, or u

<400> SEQUENCE: 12
agccatctaa ctattcccnn nnnnnnnnnn nnnnnnnnnn nnnnnnnnnn ngagcgagaa    60
attctaggt                                                            69

<210> SEQ ID NO 13
<211> LENGTH: 45
<212> TYPE: DNA
<213> ORGANISM: Artificial
<220> FEATURE:
<223> OTHER INFORMATION: BASED ON MAMMALIAN
<220> FEATURE:
<221> NAME/KEY: misc_feature
<222> LOCATION: (38)..(39)
<223> OTHER INFORMATION: (spacer 18)x5 (18-atom hexaethyleneglycol
      chain)

<400> SEQUENCE: 13
aacgcaataa atgtgaagta gatcacattt taggcaccga tggct                    45

<210> SEQ ID NO 14
<211> LENGTH: 38
<212> TYPE: DNA
<213> ORGANISM: Artificial
<220> FEATURE:
<223> OTHER INFORMATION: BASED ON MAMMALIAN

<400> SEQUENCE: 14
ggtgcctaaa atgtgatcta cttcacattt attgcgtt                            38
```

<210> SEQ ID NO 15
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 15
ggcggtatgg gcatagcgta atgggaggtt ggt                33

<210> SEQ ID NO 16
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 16
ggatgcgtaa tggttagggt gggtagggta tcc                33

<210> SEQ ID NO 17
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 17
ggatgcgtaa tggttagggt gggtagggta tcc                33

<210> SEQ ID NO 18
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 18
ggatgcgtaa tggttagggt gggtagggta tcc                33

<210> SEQ ID NO 19
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 19
gcagtaggta ctatattggc tagggtggtc tgc                33

<210> SEQ ID NO 20
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 20
gcagtaggta ctatattggc tagggtggtc tgc                33

<210> SEQ ID NO 21
<211> LENGTH: 33
<212> TYPE: DNA
<213> ORGANISM: Artificial
<220> FEATURE:

<223> OTHER INFORMATION: BASED ON MAMMALIAN

<400> SEQUENCE: 21
ggcggtatgg gcatagcgta atgggaggtc tgc                          33

<210> SEQ ID NO 22
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 22
ggatgcgtaa tggttagggt gggtagggta tcc                          33

<210> SEQ ID NO 23
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 23
ggcggtatgg gtatagcgta atgggaggtt ggt                          33

<210> SEQ ID NO 24
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 24
gggggtacta ggtattaatg ggtagggtgg tgt                          33

<210> SEQ ID NO 25
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 25
cagcagggaa cggaacggtt agggtgggta ggg                          33

<210> SEQ ID NO 26
<211> LENGTH: 33
<212> TYPE: DNA
<213> ORGANISM: Artificial
<220> FEATURE:
<223> OTHER INFORMATION: BASED ON MAMMALIAN
<220> FEATURE:
<221> NAME/KEY: misc_feature
<222> LOCATION: (5)..(5)
<223> OTHER INFORMATION: n is a, c, g, or t

<400> SEQUENCE: 26
gcggngatag gtcgcgtaag ttgggtaggg tgg                          33

<210> SEQ ID NO 27
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 27

-continued caggatgggt agggtggtca gcgaagcagt agg        33

<210> SEQ ID NO 28
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 28
caacggttgg gtgaactgta gtggcttggg gtg        33

<210> SEQ ID NO 29
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 29
caggatgggt agggtggtca gcgaagcagt agg        33

<210> SEQ ID NO 30
<211> LENGTH: 32
<212> TYPE: DNA
<213> ORGANISM: Artificial
<220> FEATURE:
<223> OTHER INFORMATION: BASED ON MAMMALIAN

<400> SEQUENCE: 30
caggatgggt agggtggtca gcgaagcagt ag         32

<210> SEQ ID NO 31
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 31
ggcgagagca gcgtgatagg gtgggtaggg tgg        33

<210> SEQ ID NO 32
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 32
cagggtcagg gctagatgat gcgattaacc atg        33

<210> SEQ ID NO 33
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 33
caggatgggt agggtggtca gcgaagcagt agg        33

<210> SEQ ID NO 34
<211> LENGTH: 33
<212> TYPE: DNA

```
<213> ORGANISM: Artificial
<220> FEATURE:
<223> OTHER INFORMATION: BASED ON MAMMALIAN

<400> SEQUENCE: 34
gggggtacta ggtatcaatg ggtagggtgg tgt                                    33

<210> SEQ ID NO 35
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 35
gggggtacta ggtatcaatg ggtagggtgg tgt                                    33

<210> SEQ ID NO 36
<211> LENGTH: 33
<212> TYPE: DNA
<213> ORGANISM: Artificial
<220> FEATURE:
<223> OTHER INFORMATION: BASED ON MAMMALIAN
<220> FEATURE:
<221> NAME/KEY: misc_feature
<222> LOCATION: (27)..(27)
<223> OTHER INFORMATION: n is a, c, g, or t

<400> SEQUENCE: 36
ggagacgtaa tgggttggtt gggaagngga tcc                                    33

<210> SEQ ID NO 37
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 37
gcatacgtaa tggtccggtt ggggcgggta tgt                                    33

<210> SEQ ID NO 38
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 38
gggggtacta ggtatcaatg ggtagggtgg tgt                                    33

<210> SEQ ID NO 39
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 39
gaggggactt aggatgggta gggtggtagg ccc                                    33

<210> SEQ ID NO 40
<211> LENGTH: 33
<212> TYPE: DNA
<213> ORGANISM: Artificial
<220> FEATURE:
<223> OTHER INFORMATION: BASED ON MAMMALIAN
```

<400> SEQUENCE: 40
gggggtacta ggtatcaatg ggtagggtgg tgt                                    33

<210> SEQ ID NO 41
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 41
ggtcggggca tagtaatgct ggattgggca gct                                    33

<210> SEQ ID NO 42
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 42
gggtaggagc agtacacgct ggaatgggtc act                                    33

<210> SEQ ID NO 43
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 43
gcagtaggta ctatattggc tagggtggtc tgc                                    33

<210> SEQ ID NO 44
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 44
gggtagggtg acagggagga cggaatgggc act                                    33

<210> SEQ ID NO 45
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 45
gcagtaggta ctatattggc tagggtggtc tgc                                    33

<210> SEQ ID NO 46
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 46
gcagtaggta ctatattggc tagggtggtc tgc                                    33

<210> SEQ ID NO 47

```
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 47
gcagtaggta ctatattggc tagggtggtc tgc                                    33

<210> SEQ ID NO 48
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 48
gggggtgcta ggtattaaag ggtagggtgg tgt                                    33

<210> SEQ ID NO 49
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 49
gcagtaggta ctatgtcggg tcgggtggtc tgc                                    33

<210> SEQ ID NO 50
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 50
gggtagggtg gttgtaatag ggattgcgat                                        30

<210> SEQ ID NO 51
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 51
gggtagggtg gttgtaatag ggattgcgat                                        30

<210> SEQ ID NO 52
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 52
ggcacaaccc gatatggcta tgaatctgcc                                        30

<210> SEQ ID NO 53
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 53
```

```
gggtagggtg gttgtaatag ggattgcgat                                              30

<210> SEQ ID NO 54
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 54
gggtagggtg gttgtaatag ggattgcgat                                              30

<210> SEQ ID NO 55
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 55
ggtgtgggtg gttattggtg tagagcgggt                                              30

<210> SEQ ID NO 56
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 56
aatggggagg ttggggtgcg ggagagtggt                                              30

<210> SEQ ID NO 57
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 57
acgcgtagga tgggtagggt ggtcgcgtta                                              30

<210> SEQ ID NO 58
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 58
gggtagggtg gttgtaatag ggattgcgat                                              30

<210> SEQ ID NO 59
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 59
gggcgaaggt acgaagacgg atgcacgtgc                                              30

<210> SEQ ID NO 60
<211> LENGTH: 30
<212> TYPE: DNA
```

<213> ORGANISM: Artificial
<220> FEATURE:
<223> OTHER INFORMATION: BASED ON MAMMALIAN

<400> SEQUENCE: 60
aaggccgcca tctgggtccg acgagtacca        30

<210> SEQ ID NO 61
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 61
tagggtgggt agggtggtca actatggggg        30

<210> SEQ ID NO 62
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 62
gggtggctgg tcaaggagat agtacgatgc        30

<210> SEQ ID NO 63
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 63
ggtagggtgg ttaaaatagg ggaatggcag        30

<210> SEQ ID NO 64
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 64
cacaagaagg gcgagcgctg agcatagtgc        30

<210> SEQ ID NO 65
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 65
ccaacgacac atagggtaca cgccgcctcc        30

<210> SEQ ID NO 66
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 66
ggtagggtgg ttaaaatagg ggaatggcag        30

<210> SEQ ID NO 67
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 67
taggatgggt agggtggtcc caggaatggc                                    30

<210> SEQ ID NO 68
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 68
taggatgggt agggtggccc caggaatggc                                    30

<210> SEQ ID NO 69
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 69
ggtagggtgg ttaaaatagg ggaatggcag                                    30

<210> SEQ ID NO 70
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 70
gatgtggccc agaagcataa cacgacgtac                                    30

<210> SEQ ID NO 71
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 71
taggatgggt agggtggtcc caggaatggc                                    30

<210> SEQ ID NO 72
<211> LENGTH: 30
<212> TYPE: DNA
<213> ORGANISM: Artificial
<220> FEATURE:
<223> OTHER INFORMATION: BASED ON MAMMALIAN

<400> SEQUENCE: 72
ggagatgcag gtactgagta gggagtgtgc                                    30

<210> SEQ ID NO 73
<211> LENGTH: 30
<212> TYPE: DNA
<213> ORGANISM: Artificial
<220> FEATURE:

<223> OTHER INFORMATION: BASED ON MAMMALIAN

<400> SEQUENCE: 73
taggatgggt agggtggtcc caggaatggc                    30

<210> SEQ ID NO 74
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 74
aatcaagggc tggtgttaaa ggtgatcgac tag                33

<210> SEQ ID NO 75
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 75
aaggggagcc atcacacagg aggtcgcttc gct                33

<210> SEQ ID NO 76
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 76
aaaggcatca cctagagttg ccgccgatac ttg                33

<210> SEQ ID NO 77
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 77
ggggatgtgc gaaactggtg actatgcggg tgc                33

<210> SEQ ID NO 78
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 78
cgaaaggagc catcaacctt gaaacgcccg tcc                33

<210> SEQ ID NO 79
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 79
cagacgggag ccatcgacat agaggtgatt gcc                33

```
<210> SEQ ID NO 80
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 80
agggaaagcc atcacctaga cacatacagc atg                              33

<210> SEQ ID NO 81
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 81
ataagaagcc atcataggga cctagctagc ccc                              33

<210> SEQ ID NO 82
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 82
ccaacagacg gtagcacaac actagtactc tgg                              33

<210> SEQ ID NO 83
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 83
acagacgccc ctagtaaaca ataaccgatg gcc                              33

<210> SEQ ID NO 84
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 84
atagctactc gccaagggtg acttctgcta ttg                              33

<210> SEQ ID NO 85
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 85
atggggcaac gcggagacct gtcggtactg cct                              33

<210> SEQ ID NO 86
<211> LENGTH: 33
<212> TYPE: DNA
<213> ORGANISM: Artificial
<220> FEATURE:
<223> OTHER INFORMATION: BASED ON MAMMALIAN
```

<400> SEQUENCE: 86
gcaatatagc actaagcctt aactccatgg tgg    33

<210> SEQ ID NO 87
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 87
gcaaggaaaa acaagcaagc catcacgacc tag    33

<210> SEQ ID NO 88
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 88
caggcatccc aagaagtgtc agccgtttcg tgg    33

<210> SEQ ID NO 89
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 89
caacaggaga gcccgacaca cagatctggc ccc    33

<210> SEQ ID NO 90
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 90
acaagccatc acgtgaatgc cgaccggtac tgt    33

<210> SEQ ID NO 91
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 91
accgacaaac aagtcaatac gggacacgat cct    33

<210> SEQ ID NO 92
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 92
cagtgggtcg ggtcacagcc atgagtgttg ctg    33

<210> SEQ ID NO 93
<211> LENGTH: 33

```
<212> TYPE: DNA
<213> ORGANISM: Artificial
<220> FEATURE:
<223> OTHER INFORMATION: BASED ON MAMMALIAN

<400> SEQUENCE: 93
aacgggaaag ccatcaccat atttatcgtc ctg                              33

<210> SEQ ID NO 94
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 94
acgggcgcaa acaagatgta caaaagcatg gtg                              33

<210> SEQ ID NO 95
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 95
agcgggatag ggaactatcg gacaatcgtc gtg                              33

<210> SEQ ID NO 96
<211> LENGTH: 33
<212> TYPE: DNA
<213> ORGANISM: Artificial
<220> FEATURE:
<223> OTHER INFORMATION: BASED ON MAMMALIAN

<400> SEQUENCE: 96
gaggataaaa gccatcaact agaatgcgca tgg                              33
```

METHODS FOR THE SELECTION OF APTAMERS

CROSS REFERENCE TO RELATED APPLICATIONS

This application is a divisional of U.S. application Ser. No. 11/916,776, filed Dec. 6, 2007, which claims the priority of PCT Application PCT/US2006/018845, filed May 16, 2006, which claims the priority of U.S. provisional application No. 60/689,470, filed Jun. 10, 2005, all of which is hereby incorporated by reference in their entirety.

FIELD OF THE INVENTION

The present invention relates to methods for selecting aptamers. More specifically, the invention provides methods for the selection of aptamers for use in combination with another epitope binding agent such as another aptamer, an antibody, or a double stranded nucleic acid. The invention also encompasses methods for simultaneously selecting at least two aptamers that each recognize distinct epitopes on a target molecule.

BACKGROUND OF THE INVENTION

The ability to detect, label, and track a molecular target is a powerful research tool. To date, antibodies are the typical reagents used for such research. Antibodies have high specificity for their target, and often can be used for in vivo as well as in vitro applications. Producing antibodies, however, is a sensitive, expensive, and time-consuming endeavor. Polyclonal antibodies, although highly specific, are limited in supply. Monoclonal antibodies, while extremely useful for molecular biology techniques, require labor intensive, diligent cell culture work. Furthermore, if a specific antibody will be used for in vivo human studies, the antibody may require modification to avoid triggering an unwanted immune response. Despite these drawbacks, antibodies have remained the state of the art in many biological research fields.

Aptamers, or target specific nucleic acid sequences, offer an alternative to antibodies. The advent of in vitro selection of aptamers was key to demonstrating their utility. Aptamers can be selected to recognize virtually any target, and they can be synthetically engineered, greatly reducing cost and time when compared to producing antibodies. The most common method for selecting aptamers is referred to as Selex (Systematic Evolution of Ligands by Experimental Enrichment). In general, the Selex process selects target specific aptamers from a pool of randomly generated nucleic acid oligonucleotides through several rounds of selection and amplification. Despite the fact that aptamers are less expensive to make, do not require animal facilities to produce, and can be selected with simple molecular biology techniques, they remain in the background of biological research. A need exists for better aptamer selection methods, which will further increase the advantage of aptamers relative to antibodies. Moreover, although the Selex method has advanced the field of aptamer selection with respect to the selection of one aptamer, a need exists for methods involving the simultaneous selection of two or more aptamers that recognize distinct epitopes on a target molecule.

SUMMARY OF THE INVENTION

Among the several aspects of the invention, therefore, is a pair of nucleic acid constructs comprising a first nucleic acid construct and a second nucleic acid construct. The first nucleic acid construct comprises:

A-B-C-D;

the second nucleic acid construct comprises:

E-F-G-H;

wherein:
A, C, E, and G are each different DNA sequences from about 10 to about 30 nucleotides in length, A and C together comprising a sequence to prime a polymerase chain reaction for amplifying a first aptamer sequence, and E and G together comprising a sequence to prime a polymerase chain reaction for amplifying a second aptamer sequence;
B is a single-stranded random nucleotide sequence from about 20 to about 110 nucleotides in length that contains specific sequences binding to a first epitope of the target molecule;
D and H are a pair of complementary nucleotide sequences from about 2 to about 20 nucleotides in length, wherein D and H have a free energy for association from about 5.5 kcal/mole to about 8.0 kcal/mole at a temperature from approximately 21° C. to about 40° C. and at a salt concentration of approximately 1 mM to about 100 mM; and
F is a single-stranded random nucleotide sequence from about 20 to about 110 nucleotides in length that contains specific sequences binding to the second epitope of the target molecule.

Another aspect of the invention provides a method to select at least one aptamer in the presence of an epitope binding agent construct. Alternatively, the invention encompasses a method for simultaneously selecting at least two aptamers.

Other aspects and features of the invention will be in part apparent and in part pointed out hereinafter.

DETAILED DESCRIPTION OF THE PREFERRED EMBODIMENTS

Figure 3:
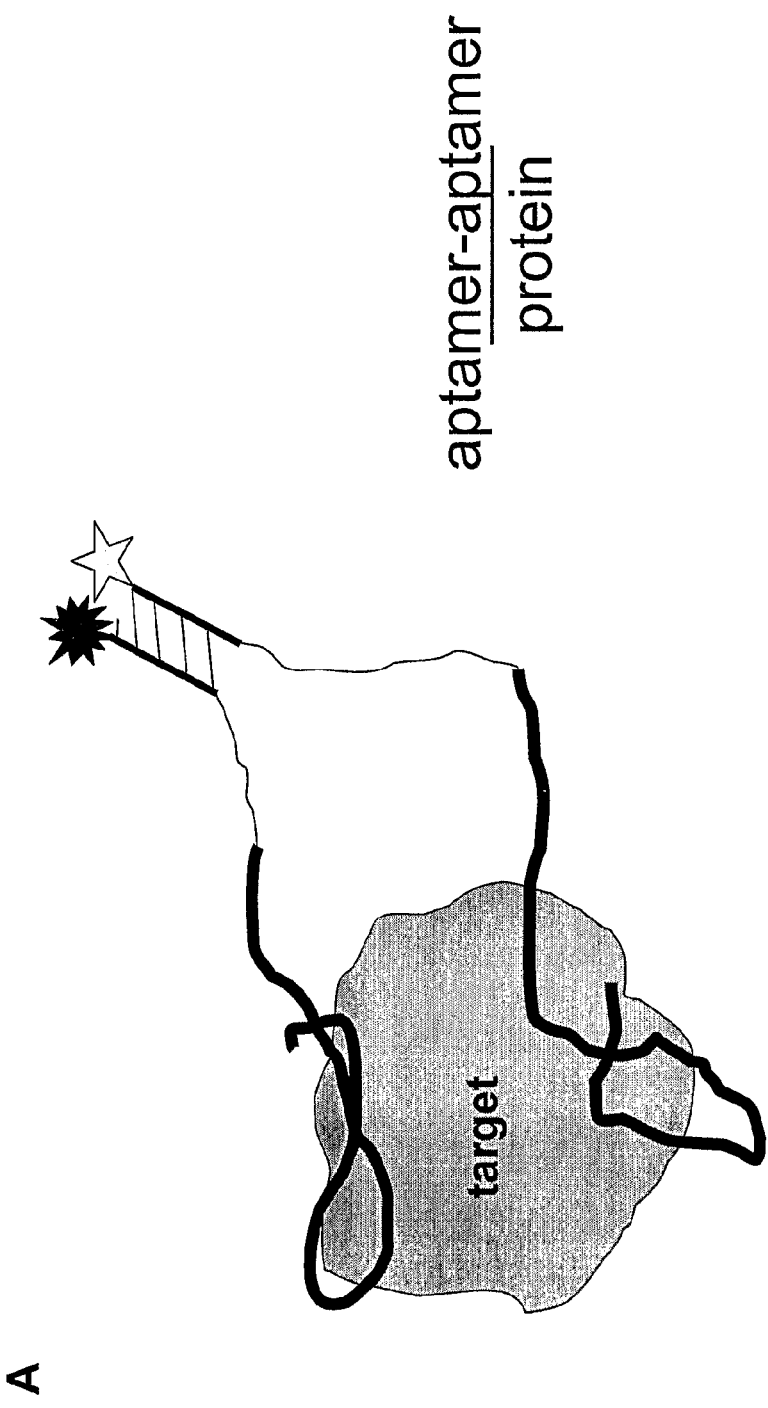
FIGS. 3A-I is a schematic illustrating various formations of molecular biosensors that can be made utilizing aptamers selected according to the invention. (A) aptamer-aptamer sensor to detect protein; (B) ds DNA-aptamer sensor to detect protein; (C) aptamer-antibody sensor to detect protein; (D) ds DNA-antibody sensor to detect protein; (E) antibody-antibody sensor to detect protein; (F) ds DNA-ds DNA sensor to detect protein; (G) ss DNA/RNA-ss DNA/RNA sensor to detect ss DNA/RNA; (H) dsDNA-protein sensor; (I) protein-protein sensor.
Figure 3:
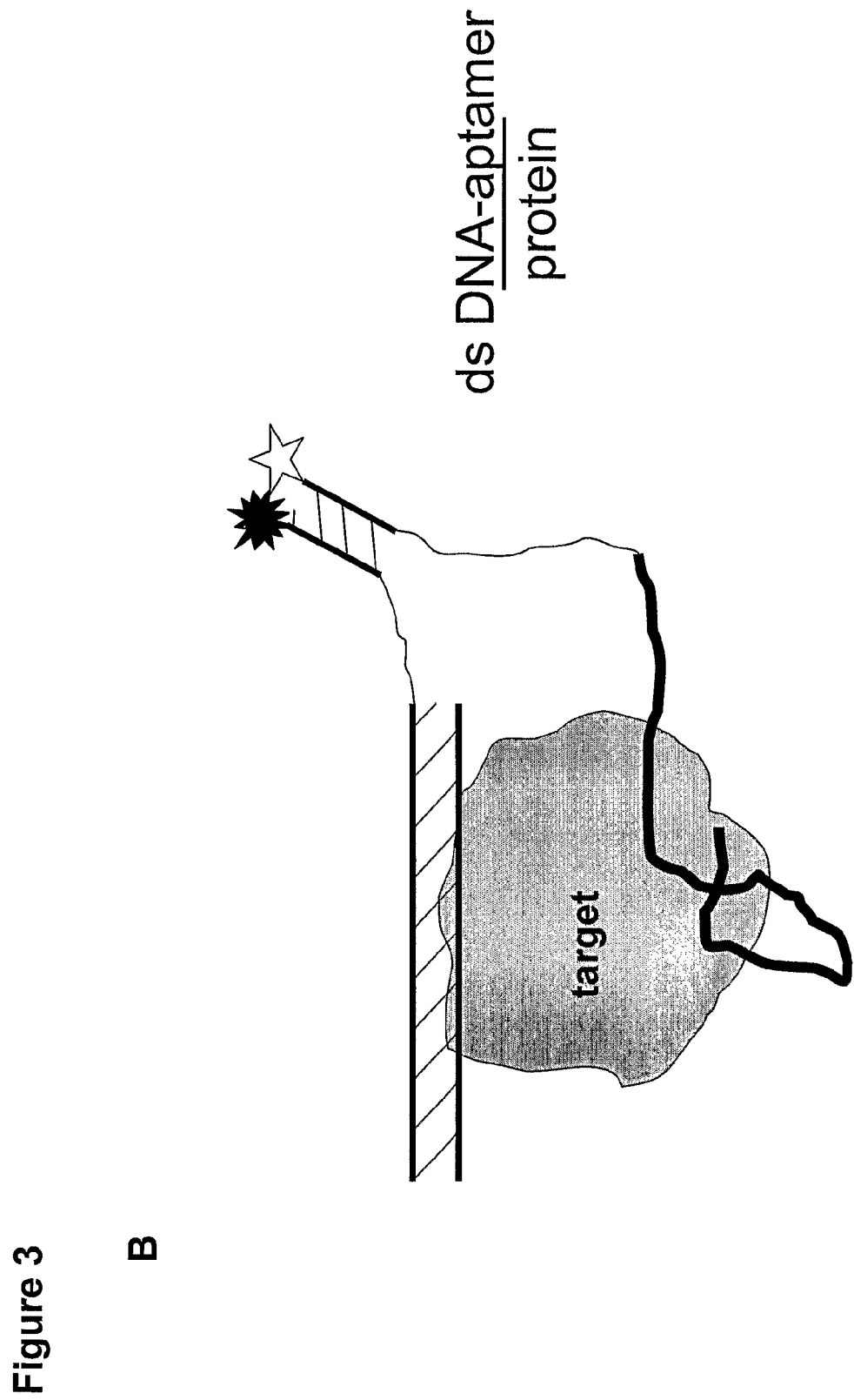
Figure 3:
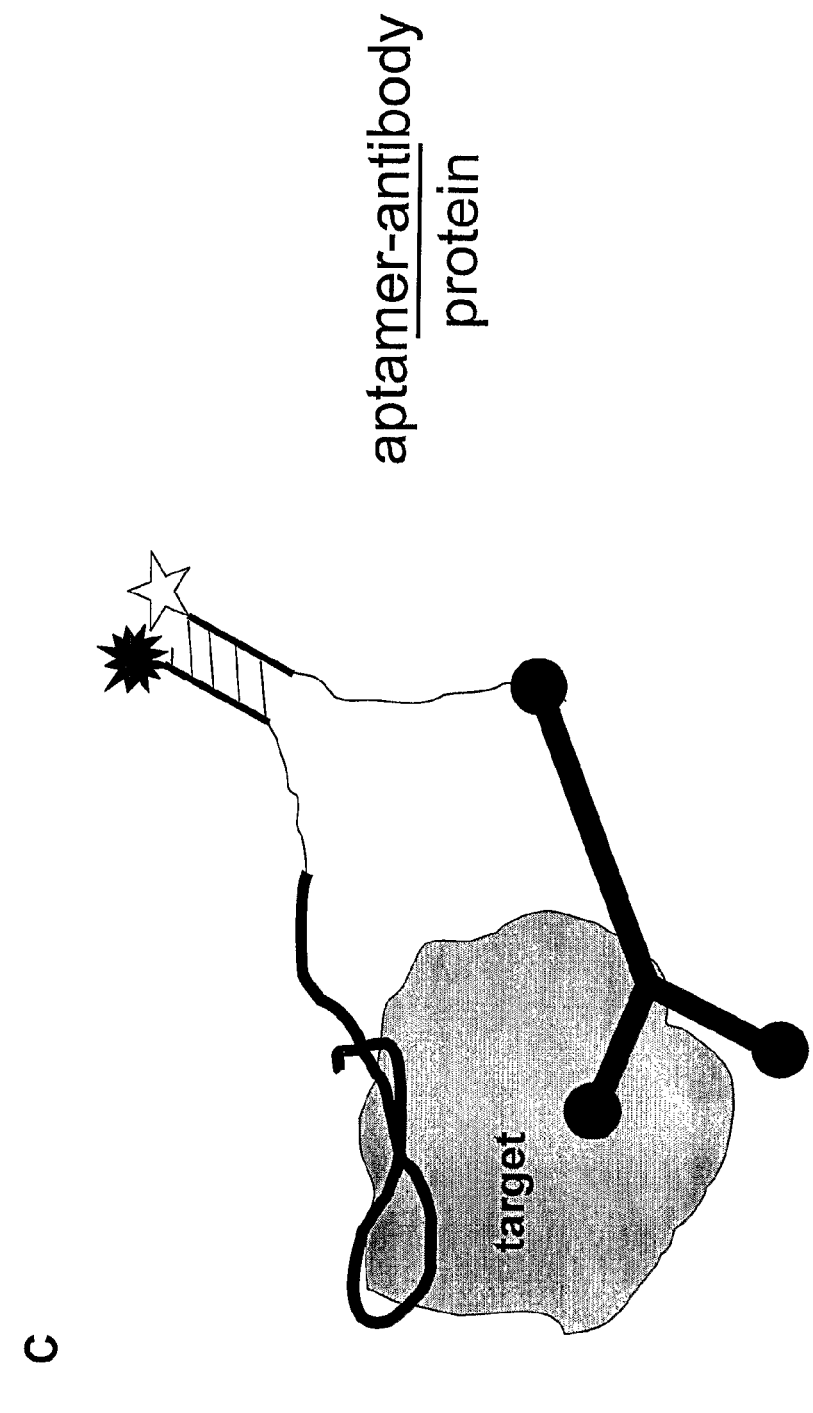
Figure 3:
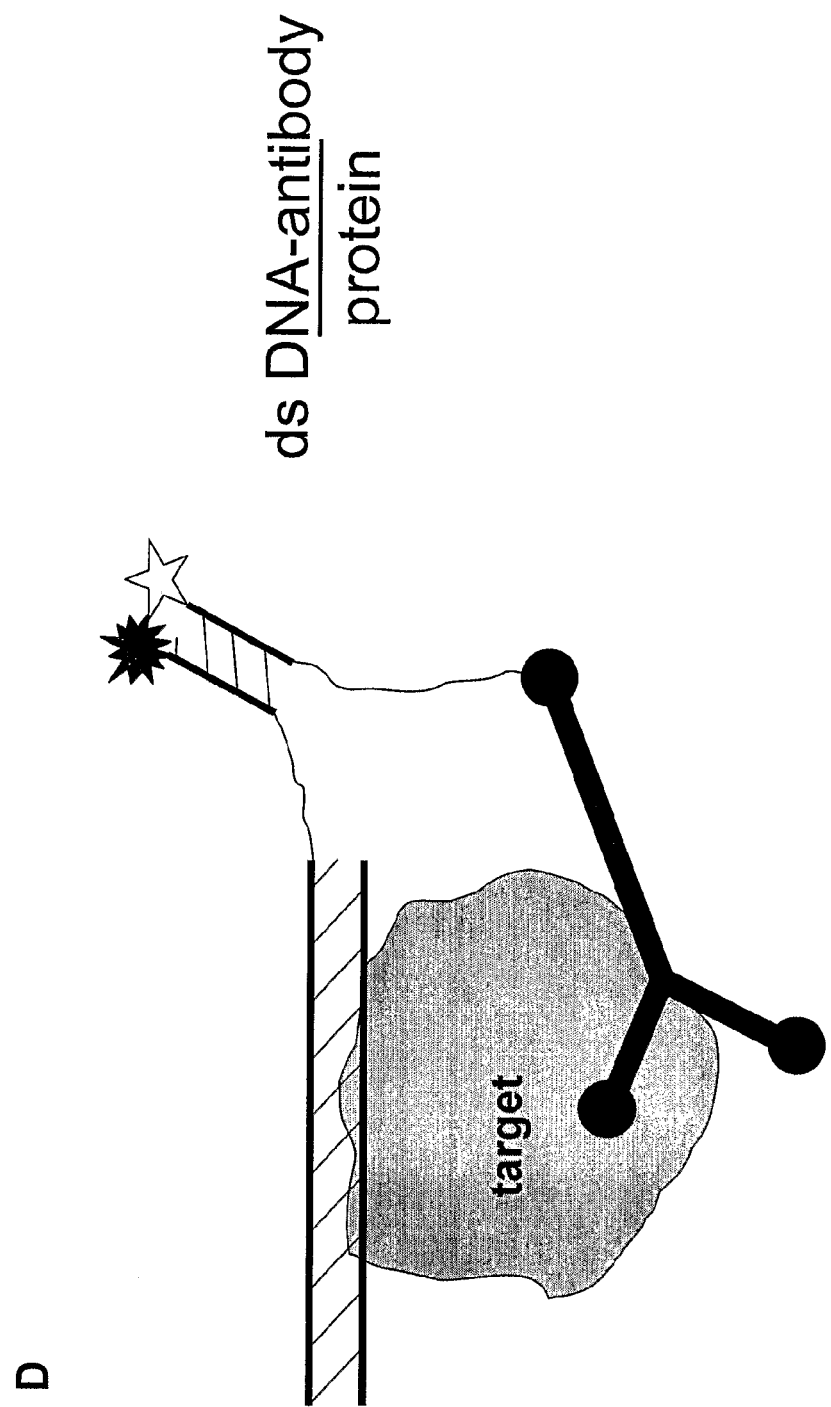
Figure 3:
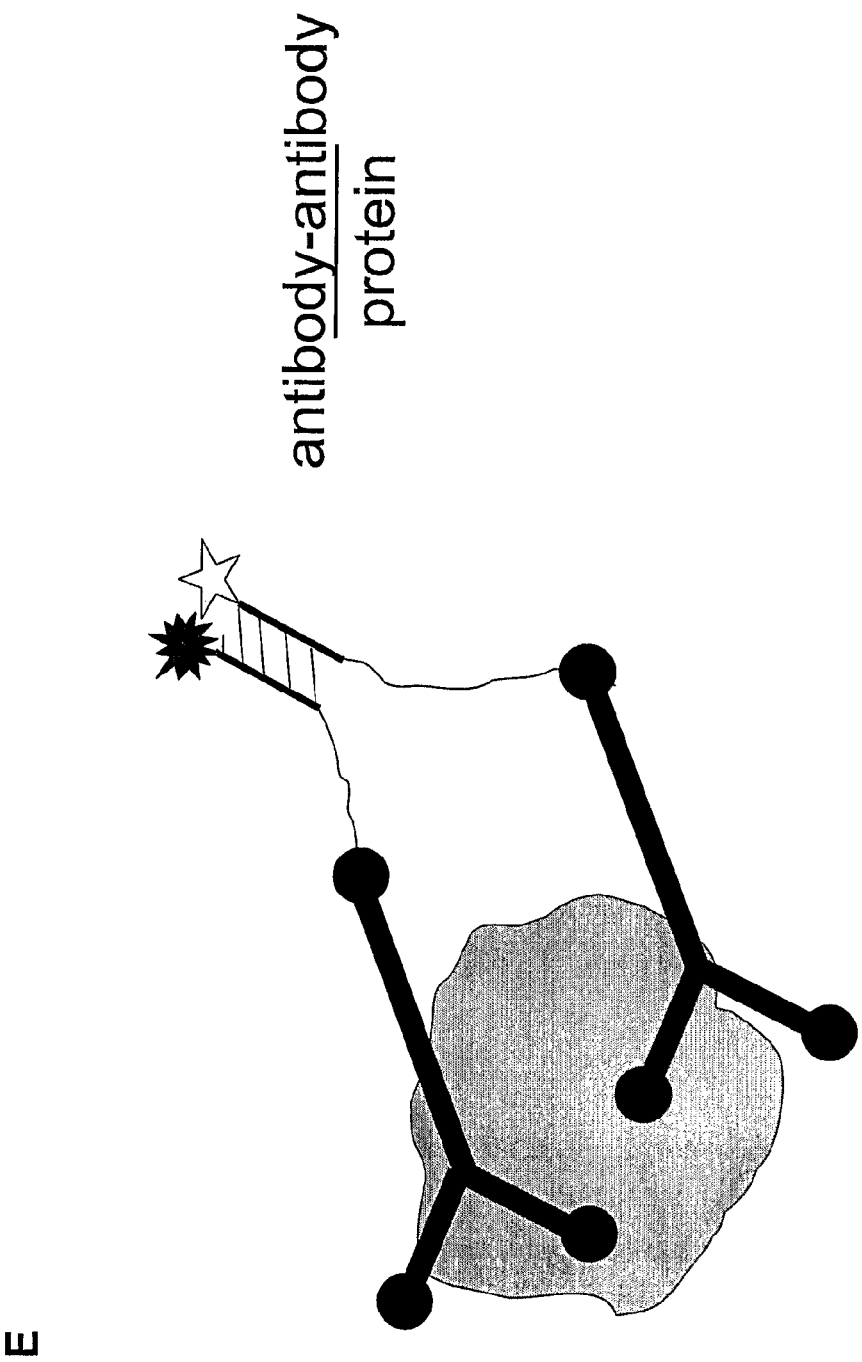
Figure 3:
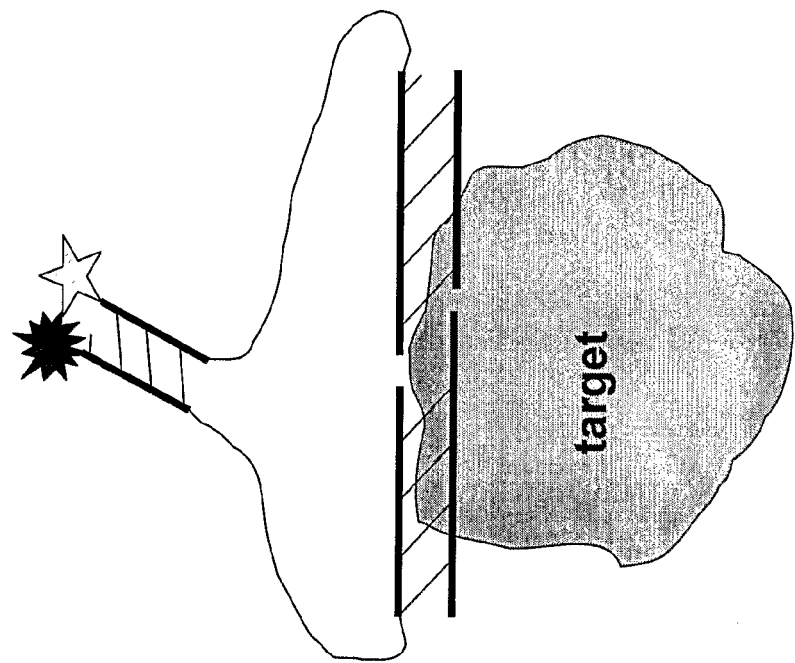
Figure 3:
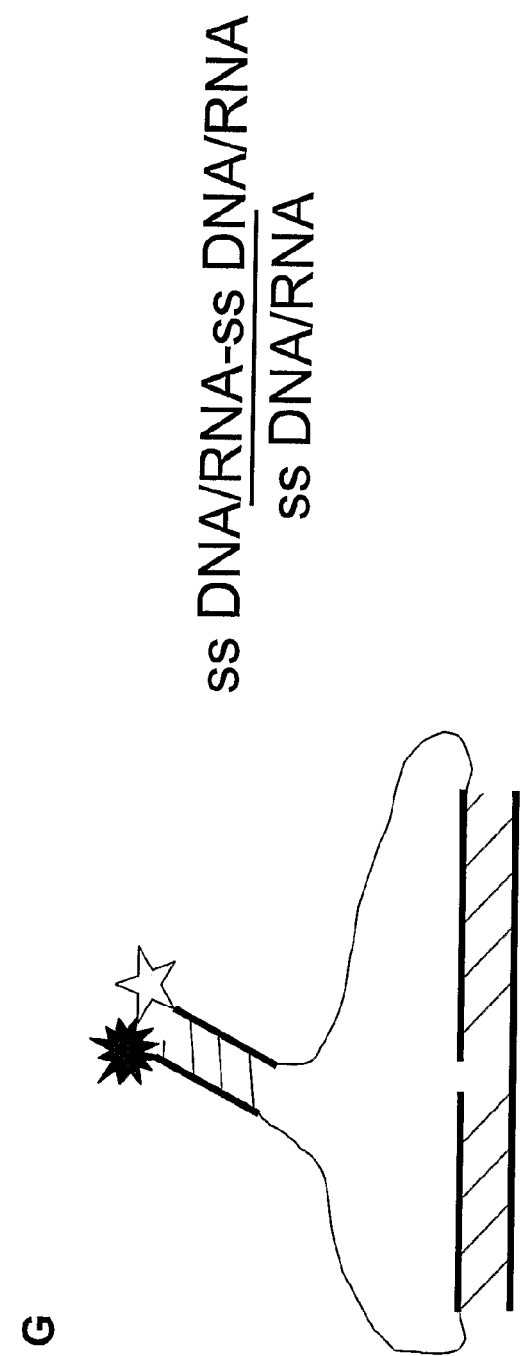
Figure 3:
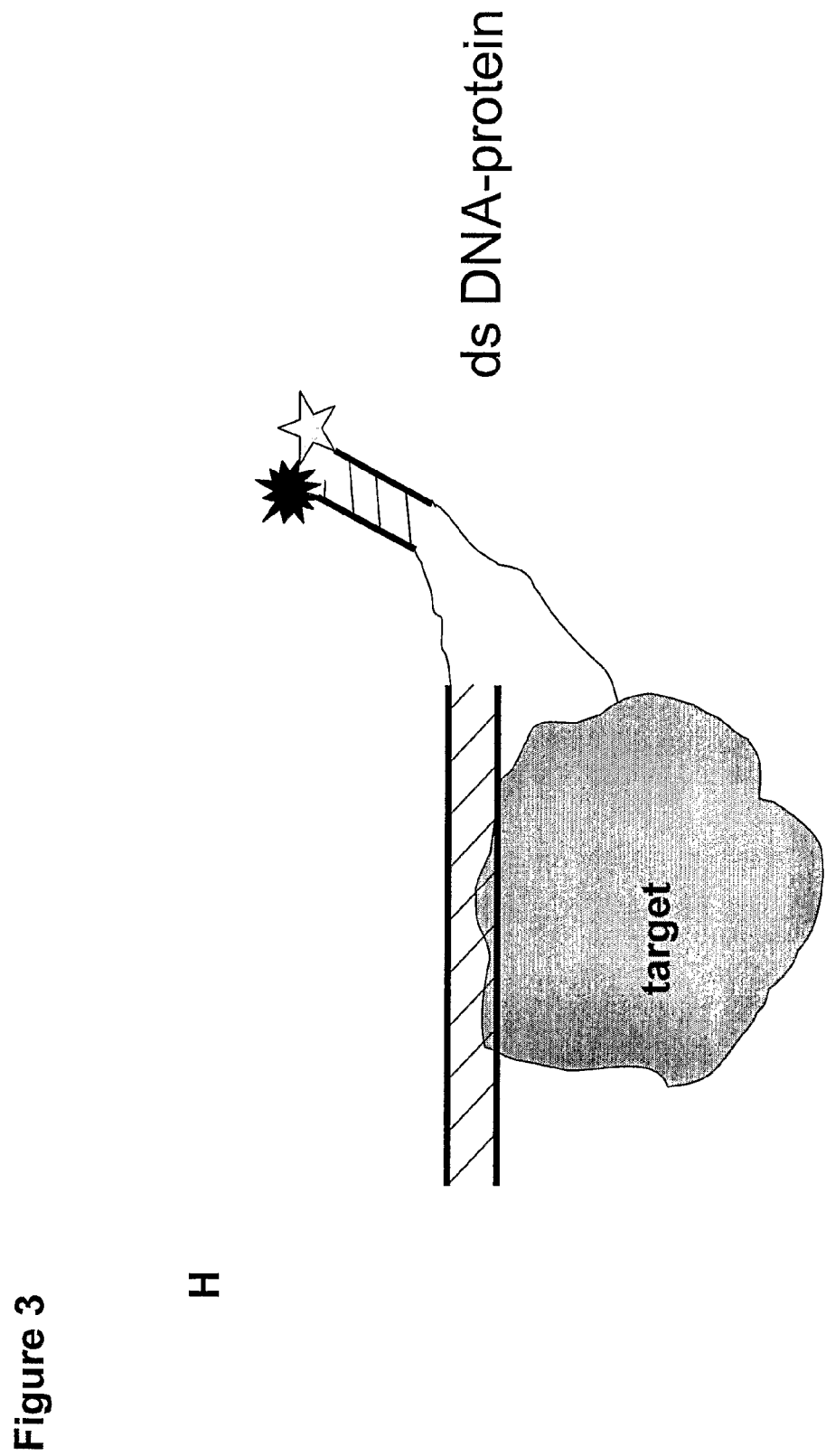
Figure 3:
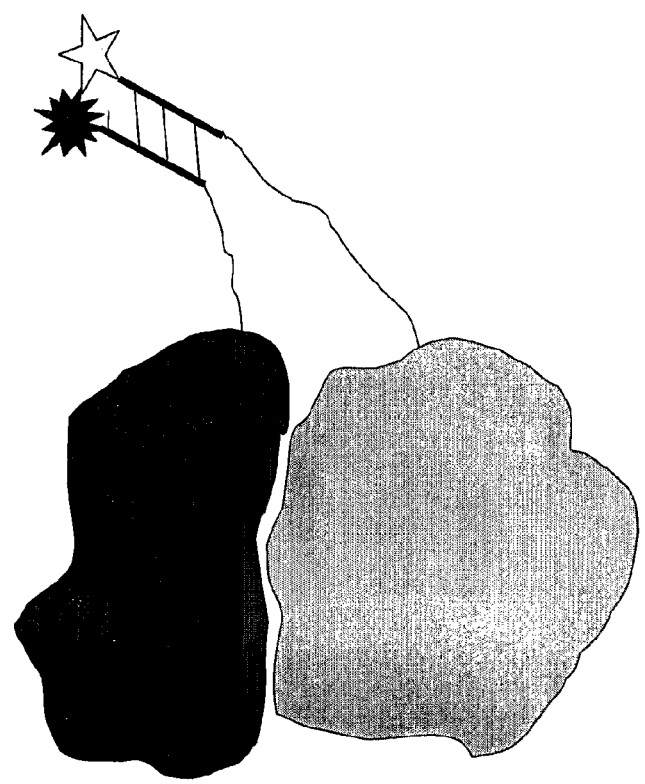
Figure 4:
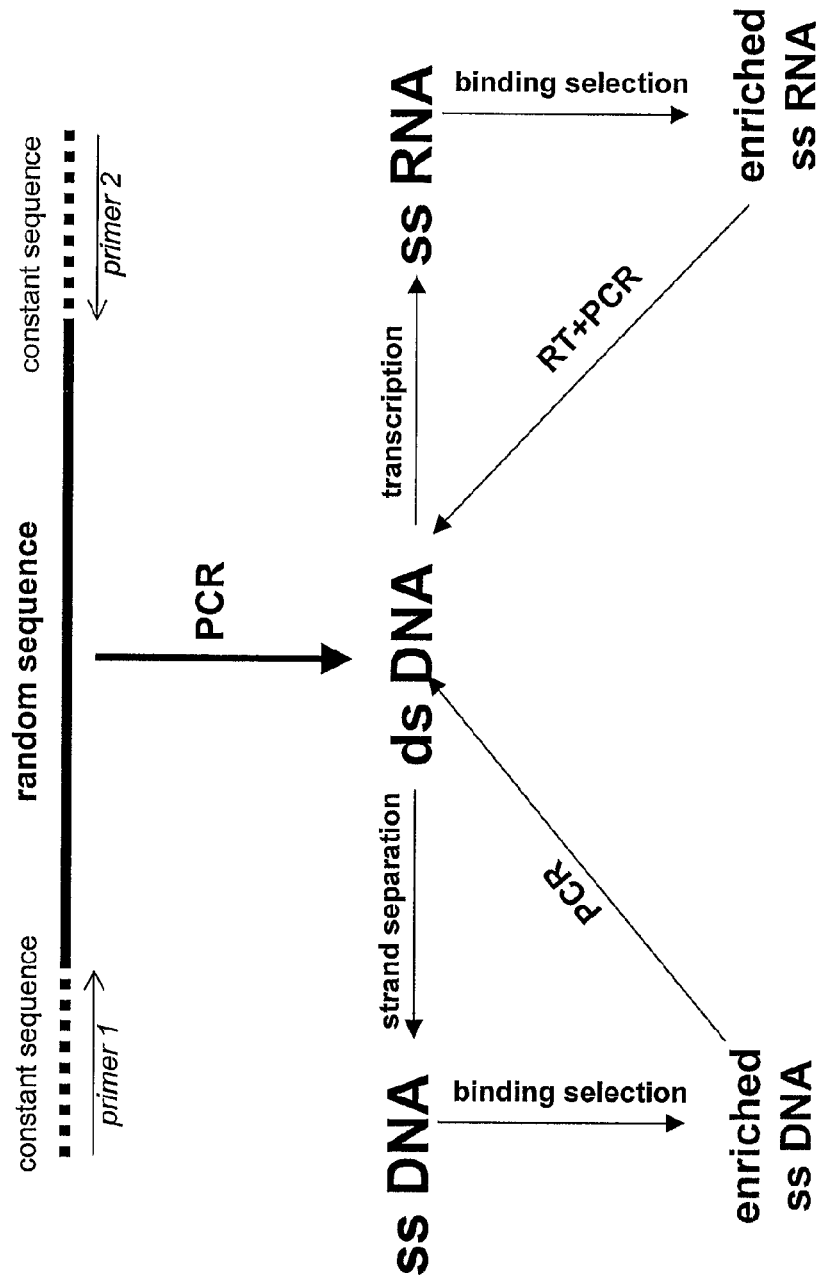
FIG. 4 is a schematic illustrating the method of the invention.

Methods for efficiently selecting aptamers have been discovered. The invention is directed to methods for simultaneously selecting two or more aptamers that each recognize distinct epitopes on a target molecule. Utilizing the method of simultaneous aptamer selection typically cuts the time of selection in half compared to methods involving sequential selection of two aptamers using Selex. Alternatively, the invention is directed to selecting at least one aptamer in the presence of an epitope binding agent construct. The aptamer and epitope binding agent construct also each recognize distinct epitopes on a target molecule. In each method of the invention, novel nucleic acid constructs are utilized to facilitate selection of aptamers having the desired epitope binding characteristics. In each aspect of the invention, the nucleic constructs comprise the aptamer or aptamers selected by the method of the invention. Advantageously, the methods of the invention may be utilized to select aptamers to construct various molecular biosensors as illustrated in FIG. 3.

(A) Method for Selection of an Aptamer in the Presence of an Epitope Binding Agent Construct One aspect of the invention encompasses a method for selecting an aptamer in the presence of an epitope binding agent construct. The aptamer and epitope binding agent construct are selected so that they each bind to the same target at two distinct epitopes. Typically, the method comprises contacting a plurality of nucleic acid constructs and epitope binding agent constructs with a target molecule to form a mixture. The mixture will generally comprise complexes having target molecule bound with nucleic acid constructs and epitope binding agent constructs. According to the method, the complex is isolated from the mixture and the nucleic acid construct is purified from the complex. The aptamer selected by the method of the invention will comprise the purified nucleic acid construct.

In this method of selection, a plurality of nucleic acid constructs is utilized in the presence of the epitope binding agent construct to facilitate aptamer selection. The nucleic acid constructs comprise:

A-B-C-D

The epitope binding agent construct comprises:

P-Q-R wherein:

A and C are each different DNA sequences from about 10 to about 30 nucleotides in length, A and C together comprising a sequence to prime a polymerase chain reaction for amplifying the aptamer sequence;

B is a single-stranded random nucleotide sequence from about 20 to about 110 nucleotides in length that contains specific sequences binding to a first epitope of the target molecule;

D and R are a pair of complementary nucleotide sequences from about 2 to about 20 nucleotides in length, wherein D and R have a free energy for association from about 5.5 kcal/mole to about 8.0 kcal/mole at a temperature from approximately 21° C. to about 40° C. and at a salt concentration of approximately 1 mM to about 100 mM;

P is an epitope binding agent that binds to a second epitope on the target molecule. The epitope binding agent will vary depending upon the embodiment, but is selected from the group comprising an aptamer, an antibody, an antibody fragment, a double-stranded DNA sequence, a ligand, a ligand fragment, a receptor, a receptor fragment, a polypeptide, a peptide, a coenzyme, a coregulator, an allosteric molecule, and an ion; and Q is a flexible linker.

Generally speaking, A and C are each different DNA sequences ranging from about 7 to about 35 nucleotides in length and function as polymerase chain reaction primers to amplify the nucleic acid construct. In another embodiment, A and C range from about 15 to about 25 nucleotides in length. In yet another embodiment, A and C range from about 15 to about 20 nucleotides in length. In still another embodiment, A and C range from about 16 to about 18 nucleotides in length. In an exemplary embodiment, A and C are 18 nucleotides in length. Typically, A and C have an average GC content from about 53% to 63%. In another embodiment, A and C have an average GC content from about 55% to about 60%. In a preferred embodiment, A and C will have an average GC content of about 60%.

B is typically a single-stranded oligonucleotide synthesized by randomly selecting and inserting a nucleotide base (A, C, T, G in the case of DNA, or A, C, U, G in the case of RNA) at every position of the oligonucleotide. In one embodiment, B encodes an aptamer sequence that binds to the first epitope on the target. In another embodiment B is comprised of DNA bases. In yet another embodiment, B is comprised of RNA bases. In another embodiment, B is comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). In a further embodiment, B is about 20 to 110 nucleotides in length. In another embodiment, B is from about 25 to about 75 nucleotides in length. In yet another embodiment, B is from about 30 to about 60 nucleotides in length.

In one embodiment, D and R are complementary nucleotide sequences from about 2 to about 20 nucleotides in length. In another embodiment, D and R are from about 4 to about 15 nucleotides in length. In a preferred embodiment, D and R are from about 5 to about 7 nucleotides in length. In one embodiment, D and R have a free energy for association from about 5.2 kcal/mole to about 8.2 kcal/mole as measured in the selection buffer conditions, defined below. In another embodiment, D and R have a free energy for association from about 6.0 kcal/mole to about 8.0 kcal/mole as measured in the selection buffer conditions defined below. In yet another embodiment, D and R have a free energy for association from about 7.0 kcal/mole to 8.0 kcal/mole in the selection buffer conditions. In a preferred embodiment, D and R have a free energy for association of 7.5 kcal/mole in the selection buffer conditions described below.

Q may be a nucleotide sequence from about 10 to about 100 nucleotides in length. In one embodiment, Q is from 10 to about 25 nucleotides in length. In another embodiment, Q is from about 25 to about 50 nucleotides in length. In a further embodiment, Q is from about 50 to about 75 nucleotides in length. In yet another embodiment, Q is from about 75 to about 100 nucleotides in length. In each embodiment, the nucleotides may be any of the nucleotide bases in DNA or RNA (A, C, T, G in the case of DNA, or A, C, U, G in the case of RNA). In one embodiment Q is comprised of DNA bases. In another embodiment, Q is comprised of RNA bases. In yet another embodiment, Q is comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). In a further embodiment, B may comprise nucleotide mimics Examples of nucleotide mimics include locked nucleic acids (LNA), peptide nucleic acids (PNA), and phosphorodiamidate morpholino oligomers (PMO). Alternatively, Q may be a polymer of bifunctional chemical linkers. In one embodiment the bifunctional chemical linker is heterobifunctional. Suitable heterobifunctional chemical linkers include sulfoSMCC (Sulfosuccinimidyl-4-(N-maleimidomethyl)cyclohexane-1-carboxylate), and lc-SPDP (N-Succinimidyl-6-(3'-(2-PyridylDithio)-Propionamido)-hexanoate). In another embodiment the bifunctional chemical linker is homobifunctional. Suitable homobifunctional linkers include disuccinimidyl suberate, disuccinimidyl glutarate, and disuccinimidyl tartrate. Additional suitable linkers are illustrated in the Examples, such as the phosphoramidate form of Spacer 18 comprised of polyethylene glycol. In one embodiment, Q is from 0 to about 500 angstroms in length. In another embodiment, Q is from about 20 to about 400 angstroms in length. In yet another embodiment, Q is from about 50 to about 250 angstroms in length.

In a preferred embodiment, A and C are approximately 18 nucleotides in length and have an average GC content of about 60%; B is about 30 to about 60 nucleotides in length; Q is a linker comprising a nucleotide sequence that is from about 10 to 100 nucleotides in length or a bifunctional chemical linker; and D and R range from about 5 to about 7 nucleotides in length and have a free energy of association of about 7.5 kcal/mole.

As will be appreciated by those of skill in the art, the choice of epitope binding agent, P, can and will vary depending upon the particular target molecule. By way of example, when the target molecule is a protein P may be an aptamer, peptide, or antibody. By way of further example, when P is double stranded nucleic acid the target molecule is typically a macromolecule that binds to DNA or a DNA binding protein. Suitable epitope binding agents, depending upon the target molecule, include agents selected from the group consisting of an aptamer, an antibody, an antibody fragment, a double-stranded DNA sequence, a ligand, a ligand fragment, a receptor, a receptor fragment, a polypeptide, a peptide, a coenzyme, a coregulator, an allosteric molecule, and an ion. In an exemplary embodiment, P is an aptamer sequence ranging in length from about 20 to about 110 bases. In another embodiment, P is an antibody selected from the group consisting of polyclonal antibodies, ascites, Fab fragments, Fab' fragments, monoclonal antibodies, and humanized antibodies. In a preferred embodiment, P is a monoclonal antibody. In an additional embodiment, P is a double stranded DNA.

Typically in the method, a plurality of nucleic acid constructs, A-B-C-D, are contacted with the epitope bind agent construct, P-Q-R, and the target molecule in the presence of a selection buffer to form a mixture. Several selection buffers are suitable for use in the invention. A suitable selection buffer is typically one that facilitates non-covalent binding of the nucleic acid construct to the target molecule in the presence of the epitope binding agent construct. In one embodiment, the selection buffer is a salt buffer with salt concentrations from about 1 mM to 100 mM. In another embodiment, the selection buffer is comprised of Tris-HCl, NaCl, KCl, and $MgCl_2$. In a preferred embodiment, the selection buffer is comprised of 50 mM Tris-HCl, 100 mM NaCl, 5 mM KCl, and 1 mM $MgCl_2$. In one embodiment, the selection buffer has a pH range from about 6.5 to about 8.5. In another embodiment, the selection buffer has a pH range from about 7.0 to 8.0. In a preferred embodiment, the pH is 7.5. Alternatively, the selection buffer may additionally contain analytes that assist binding of the constructs to the target molecule. Suitable examples of such analytes can include, but are not limited to, protein co-factors, DNA-binding proteins, scaffolding proteins, or divalent ions.

The mixture of the plurality of nucleic acid constructs, epitope binding agent constructs and target molecules are incubated in selection buffer from about 10 to about 45 min. In yet another embodiment, the incubation is performed for about 15 to about 30 min. Typically, the incubation is performed at a temperature range from about 21° C. to about 40° C. In another embodiment, the incubation is performed at a temperature range from about 20° C. to about 30° C. In yet another embodiment, the incubation is performed at 35° C. In a preferred embodiment, the incubation is performed at 25° C. for about 15 to about 30 min. Generally speaking after incubation, the mixture will typically comprise complexes of the target molecule having nucleic acid construct bound to a first epitope and epitope binding agent construct bound to a second epitope of the target molecule. The mixture will also comprise unbound nucleic acid constructs and epitope binding agent constructs.

The complex comprising the target molecule having bound nucleic acid construct and bound epitope binding agent construct is preferably isolated from the mixture. In one embodiment, nitrocellulose filters are used to separate the complex from the mixture. In an alternative embodiment magnetic beads are used to separate the complex from the mixture. In yet another embodiment sepharose beads can be used to separate the complex from the mixture. In an exemplary embodiment, strepavidin-linked magnetic beads are used to separate the complex from the mixture.

Optionally, the target molecules are subjected to denaturation and then the nucleic acid constructs purified from the complex. In one embodiment, urea is used to denature the target molecule. In a preferred embodiment, 7M urea in 1M NaCl is used to denature the target molecule. The nucleic acid constructs may be purified from the target molecule by precipitation. In another embodiment, the nucleic acid constructs are precipitated with ethanol. In yet another embodiment, the nucleic acid constructs are precipitated with isopropanol. In one embodiment, the precipitated DNA is resuspended in water. Alternatively, the precipitated DNA is resuspended in TE buffer.

Generally speaking, the purified, resuspended nucleic acid constructs are then amplified using the polymerase chain reaction (PCR). If the nucleic acid construct contains a B comprised of RNA bases, reverse transcriptase is preferably used to convert the RNA bases to DNA bases before initiation of the PCR. The PCR is performed with primers that recognize both the 3' and the 5' end of the nucleic acid constructs in accordance with methods generally known in the art. In one embodiment, either the 3' or 5' primer is attached to a fluorescent probe. In an alternative embodiment, either the 3' or the 5' primer is attached to fluorescein. In another embodiment, either the 3' or 5' primer is biotinylated. In a preferred embodiment, one primer is labeled with fluorescein, and the other primer is biotinylated.

In addition to primers, the PCR reaction contains buffer, deoxynucleotide triphosphates, polymerase, and template nucleic acid. In one embodiment, the PCR can be performed with a heat-stable polymerase. In a preferred embodiment, the concentrations of PCR reactants are outlined in the examples section as follows: 80 uL of dd H2O, 10 uL of 10×PCR buffer, 6 uL of $MgCl_2$, 0.8 uL 25 mM dNTPs, 1 uL 50 uM primer 1 (modified with fluorescein), 1 uL 50 uM primer 2 (biotinylated), 0.5 uL Taq polymerase, and 1 uL of template.

In another embodiment, the PCR consists of a warm-up period, where the temperature is held in a range between about 70° C. and about 74° C. Subsequently, the PCR consists of several cycles (about 8 to about 25) of 1) incubating the reaction at a temperature between about 92° C. and about 97° C. for about 20 sec to about 1 min; 2) incubating the reaction at a temperature between about 48° C. and about 56° C. for about 20 sec to about 1 min; and 3) incubating the reaction at a temperature between about 70° C. and about 74° C. for about 45 sec to about 2 min. After the final cycle, the PCR is concluded with an incubation between about 70° C. and about 74° C. for about 3 min to about 10 min. In an alternative embodiment, the reaction consists of 12-18 cycles. A preferred embodiment of the PCR, as outlined in the examples section, is as follows: 5 min at 95° C., sixteen cycles of 30 s at 95° C., 30 s at 50° C., and 1 min at 72° C., and then an extension period of 5 min at 72° C.

Typically after PCR amplification, the double-stranded DNA PCR product is separated from the remaining PCR reactants. One exemplary embodiment for such separation is subjecting the PCR product to agarose gel electrophoresis. In another embodiment, the PCR product is separated in a low melting point agarose gel. In a preferred embodiment, the gel is a native 10% acrylamide gel made in TBE buffer. In one embodiment, the band(s) having the double-stranded DNA PCR product are visualized in the gel by ethidium bromide staining. In another embodiment, the band(s) are visualized by fluorescein fluorescence. Irrespective of the embodiment, the bands are typically excised from the gel by methods generally known in the art.

Generally speaking, the double-stranded gel-purified PCR product is separated into single-stranded DNA in accordance with methods generally known in the art. One such embodiment involves using a basic pH to denature the double helix. In another embodiment, 0.15N NaOH is used to denature the helix. In still another embodiment, streptavidin linked beads are used to separate the denatured DNA strands. In a preferred embodiment, magnetic streptavidin beads are used to separate the denatured DNA strands.

The method of the invention typically involves several rounds of selection, separation, amplification and purification in accordance with the procedures described above until nucleic acid constructs having the desired binding affinity for the target molecule are selected. In accordance with the method, the single-stranded DNA of estimated concentration is used for the next round of selection. In one embodiment, the cycle of selection, separation, amplification, purification, and strand separation is performed from about 4 to about 20 times. In another embodiment, the said cycle is performed from about 12 to about 18 times. In yet another embodiment, the said cycle is performed until the measured binding-activity of the selected nucleic acid constructs reaches the desired strength.

Alternatively, the single DNA strand attached to the strepavidin-linked beads is used as a template for RNA polymerase. In this embodiment, after the RNA polymerase is finished, the supernatant contains the RNA nucleic acid construct that can be used in another round of RNA aptamer selection.

In an alternative method, if a RNA aptamer is being selected, the double-stranded, gel-purified PCR DNA product is transcribed with RNA polymerase to produce a single-stranded RNA construct. In such a case, A will typically contain a sequence encoding a promoter recognized by RNA polymerase. In one embodiment, double-stranded, gel-purified PCR DNA product attached to strepavidin-linked beads is used as a template for RNA polymerase. In this embodiment, after the RNA polymerase reaction, the supernatant containing the RNA nucleic acid construct can be used in another round of RNA aptamer selection.

Generally speaking, after the nucleic acid constructs have reached the desired binding specificity, the nucleic acid constructs are cloned, and the cloned DNA is sequenced. In one embodiment, the sequences are used in aptamer constructs either alone or as part of a molecular biosensor.

(B) Method for Simultaneous Selection of Two or More Aptamers

Another aspect of the invention is a method for simultaneously selecting two or more aptamers. The aptamers selected by the method each bind to the same target molecule at two distinct epitopes. Typically, the method comprises contacting a plurality of pairs of nucleic acid constructs with a target molecule to form a mixture. The mixture will generally comprise complexes having target molecule bound with a pair of nucleic acid constructs at distinct epitope sites. According to the method, the complex is isolated from the mixture and the nucleic acid constructs are purified from the complex. The aptamers selected by the method of the invention will comprise the pair of purified nucleic acid constructs.

In the method of the invention, the first nucleic acid constructs comprises:

A-B-C-D

The second nucleic acid construct comprises:

E-F-G-H.

wherein:
- A, C, E, and G are each different DNA sequences from about 10 to about 30 nucleotides in length, A and C together comprising a sequence to prime a polymerase chain reaction for amplifying a first aptamer sequence, and E and G together comprising a sequence to prime a polymerase chain reaction for amplifying a second aptamer sequence;
- B is a single-stranded random nucleotide sequence from about 20 to about 110 nucleotides in length that contains specific sequences binding to a first epitope of the target molecule;
- D and H are a pair of complementary nucleotide sequences from about 2 to about 20 nucleotides in length, wherein D and H have a free energy for association from about 5.5 kcal/mole to about 8.0 kcal/mole at a temperature from approximately 21° C. to about 40° C. and at a salt concentration of approximately 1 mM to about 100 mM; and
- F is a single-stranded random nucleotide sequence from about 20 to about 110 nucleotides in length that contains specific sequences binding to the second epitope of the target molecule.

In another embodiment, A, C, E and G are each different DNA sequences ranging from about 7 to about 35 nucleotides in length. In another embodiment, A, C, E, and G range from about 15 to about 25 nucleotides in length. In yet another embodiment, A, C, E, and G range from about 15 to about 20 nucleotides in length. In still another embodiment, A, C, E and G range from about 16 to about 18 nucleotides in length. In an exemplary embodiment, A, C, E and G are 18 nucleotides in length. Generally speaking, A, C, E and G have an average GC content from about 53% to 63%. In another embodiment, A, C, E and G have an average GC content from about 55% to about 60%. In a preferred embodiment, A, C, E and G will have an average GC content of about 60%.

In one embodiment, B and F are single-stranded oligonucleotides synthesized by randomly selecting and inserting a nucleotide base (A, C, T, G in the case of DNA, or A, C, U, G in the case of RNA) at every position of the oligonucleotide. In a preferred embodiment, B and F encode an aptamer sequence, such that B binds to the first epitope on the target molecule and F binds to the second epitope on the target molecule. In one embodiment B and F are comprised of DNA bases. In another embodiment, B and F are comprised of RNA bases. In yet another embodiment, B and F are comprised of modified nucleic acid bases, such as modified DNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). In typical embodiments, B and F are about 20 to 110 nucleotides in length. In another embodiment, B and F are from about 25 to about 75 nucleotides in length. In yet another embodiment, B and F are from about 30 to about 60 nucleotides in length.

D and H are complementary nucleotide sequences from about 2 to about 20 nucleotides in length. In another embodiment, D and H are from about 4 to about 15 nucleotides in length. In a preferred embodiment, D and H are from about 5 to about 7 nucleotides in length. In one embodiment, D and H have a free energy for association from about 5.2 kcal/mole to about 8.2 kcal/mole as measured in the selection buffer conditions, defined below. In another embodiment, D and H have a free energy for association from about 6.0 kcal/mole to about 8.0 kcal/mole as measured in the selection buffer conditions. In yet another embodiment, D and H have a free energy for association from about 7.0 kcal/mole to 8.0 kcal/mole in the selection buffer conditions. In a preferred embodiment, D and H have a free energy for association of 7.5 kcal/mole in the selection buffer conditions.

In a preferred embodiment, A, C, E and G are approximately 18 nucleotides in length and have an average GC content of about 60%, B and F are about 30 to about 60 nucleotides in length, and D and H range from about 5 to about 7 nucleotides in length and have a free energy of association of about 7.5 kcal/mole.

The method for simultaneous selection is initiated by contacting a plurality of pairs of the nucleic acid constructs A-B-C-D and E-F-G-H with the target molecule in the presence of a selection buffer to form a complex. Generally speaking, suitable selection buffers allow non-covalent simultaneous binding of the nucleic acid constructs to the target molecule. The method for simultaneous selection then involves the same steps of selection, separation, amplification and purification as described in section (a) above involving methods for the selection of an aptamer in the presence of an epitope binding agent construct, with the exception that the PCR is designed to amplify both nucleic acid constructs (A-B-C-D and E-F-G-H), using primers to A, C, E, and G. Typically several rounds of selection are performed until pairs of nucleic acid constructs having the desired affinity for the target molecule are selected. In one embodiment, the cycle of selection, separation, amplification, purification, and strand separation is performed from about 4 to about 20 times. In another embodiment, the cycle is performed from about 12 to about 18 times.

After the pair of nucleic acid constructs has reached the desired binding specificity, the nucleic acid constructs are cloned, and the cloned DNA is sequenced. The resulting nucleic acid constructs comprise a first aptamer that binds to a first epitope on the target molecule and a second aptamer that binds to a second epitope on the target molecule.

In another aspect of the invention, two aptamers can be simultaneously selected in the presence of a bridging construct comprised of S-T-U. In one embodiment, S and U are complementary nucleotide sequences from about 2 to about 20 nucleotides in length. In another embodiment, S and U are from about 4 to about 15 nucleotides in length. In a preferred embodiment, S and U are from about 5 to about 7 nucleotides in length. In one embodiment, S and U have a free energy for association from about 5.2 kcal/mole to about 8.2 kcal/mole as measured in the selection buffer conditions, defined below. In another embodiment, S and U have a free energy for association from about 6.0 kcal/mole to about 8.0 kcal/mole as measured in the selection buffer conditions. In yet another embodiment, S and U have a free energy for association from about 7.0 kcal/mole to 8.0 kcal/mole in the selection buffer conditions. In a preferred embodiment, S and U have a free energy for association of 7.5 kcal/mole in the selection buffer conditions.

T may be a nucleotide sequence from about 10 to about 100 nucleotides in length. In one embodiment, T is from 10 to about 25 nucleotides in length. In another embodiment, T is from about 25 to about 50 nucleotides in length. In a further embodiment, T is from about 50 to about 75 nucleotides in length. In yet another embodiment, T is from about 75 to about 100 nucleotides in length. In each embodiment, the nucleotides may be any of the nucleotide bases in DNA or RNA (A, C, T, G in the case of DNA, or A, C, U, G in the case of RNA). In one embodiment T is comprised of DNA bases. In another embodiment, T is comprised of RNA bases. In yet another embodiment, T is comprised of modified nucleic acid bases, such as modified DNA bases or modified RNA bases. Modifications may occur at, but are not restricted to, the sugar 2' position, the C-5 position of pyrimidines, and the 8-position of purines. Examples of suitable modified DNA or RNA bases include 2'-fluoro nucleotides, 2'-amino nucleotides, 5'-aminoallyl-2'-fluoro nucleotides and phosphorothioate nucleotides (monothiophosphate and dithiophosphate). In a further embodiment, B may comprise nucleotide mimics Examples of nucleotide mimics include locked nucleic acids (LNA), peptide nucleic acids (PNA), and phosphorodiamidate morpholino oligomers (PMO). Alternatively, T may be a polymer of bifunctional chemical linkers. In one embodiment the bifunctional chemical linker is heterobifunctional. Suitable heterobifunctional chemical linkers include sulfoSMCC (Sulfosuccinimidyl-4-(N-maleimidomethyl)cyclohexane-1-carboxylate), and lc-SPDP (N-Succinimidyl-6-(3'-(2-PyridylDithio)-Propionamido)-hexanoate). In another embodiment the bifunctional chemical linker is homobifunctional. Suitable homobifunctional linkers include disuccinimidyl suberate, disuccinimidyl glutarate, and disuccinimidyl tartrate. Additional suitable linkers are illustrated in the Examples, such as the phosphoramidate form of Spacer 18 comprised of polyethylene glycol. In one embodiment, T is from 0 to about 500 angstroms in length. In another embodiment, T is from about 20 to about 400 angstroms in length. In yet another embodiment, T is from about 50 to about 250 angstroms in length.

In one embodiment, S is complementary to D and U is complementary to H. In another embodiment, S and U will not bind to D and H unless S, U, D, and H are brought in close proximity by the A-B-C-D construct and the E-F-G-H construct binding to the target.

In this embodiment of the invention utilizing the bridging construct, the method is initiated in the presence of nucleic acid constructs A-B-C-D and E-F-G-H, and the bridging construct S-T-U. Generally speaking, the method is performed as described with the same steps detailed above. In one embodiment, after the final round of selection, but before cloning, the bridging construct is ligated to the A-B-C-D construct and the E-F-G-H construct. This embodiment allows the analysis of pairs of selected nucleic acid sequences that are best suited for use in a molecular biosensor.

DEFINITIONS

As used herein, the term "analyte" refers generally to a ligand, chemical moiety, compound, ion, salt, metal, enzyme, secondary messenger of a cellular signal transduction pathway, drug, nanoparticle, environmental contaminant, toxin, fatty acid, steroid, hormone, carbohydrate, amino acid, peptide, polypeptide, protein or other amino acid polymer, microbe, virus or any other agent which is capable of binding to a polypeptide, protein or macromolecular complex in such a way as to create an epitope or alter the availability of an epitope for binding to an aptamer.

The term "aptamer" refers to a polynucleotide, generally a RNA, modified RNA, DNA, or modified DNA that has a useful biological activity in terms of biochemical activity, molecular recognition or binding attributes. Usually, an aptamer has a molecular activity such as binding to a target molecule at a specific epitope (region).

The term "epitope" refers generally to a particular region of a target molecule. Examples include an antigen, a hapten, a molecule, a polymer, a prion, a microbe, a cell, a peptide, polypeptide, protein, or macromolecular complex. An epitope may consist of a small peptide derived from a larger polypeptide. An epitope may be a two or three-dimensional surface or surface feature of a polypeptide, protein or macromolecular complex that comprises several non-contiguous peptide stretches or amino acid groups.

The term "epitope binding agent" refers to a substance that is capable of binding to a specific epitope of an antigen, a polypeptide, a protein or a macromolecular complex. Non-limiting examples of epitope binding agents include aptamers, thioaptamers, double-stranded DNA sequence, peptides and polypeptides, ligands and fragments of ligands, receptors and fragments of receptors, antibodies and fragments of antibodies, polynucleotides, coenzymes, coregulators, allosteric molecules, peptide nucleic acids, locked nucleic acids, phosphorodiamidate morpholino oligomers (PMO), and ions.

The term "epitope binding agent construct" refers to a construct that contains an epitope-binding agent and can serve in a "molecular biosensor" with another epitope binding agent construct. Preferably, an epitope binding agent construct also contains a "linker," and a "signaling oligo". Epitope binding agent constructs can be used to initiate the aptamer selection methods of the invention. An aptamer construct is a special kind of epitope binding agent construct wherein the epitope binding agent is an aptamer.

The term "molecular biosensor" refers to a construct comprised of at least two epitope binding agent constructs. The molecular biosensor can be used for detecting or quantifying the presence of a target molecule.

The term "nucleic acid construct" refers to a molecule comprising a random nucleic acid sequence flanked by two primers. Preferably, a nucleic acid construct also contains a signaling oligo. Nucleic acid constructs are used to initiate the aptamer selection methods of the invention.

The term "signaling oligo" means a short (generally 2 to 15 nucleotides, preferably 5 to 7 nucleotides in length) single-stranded polynucleotide. Signaling oligos are typically used in pairs comprising a first signaling oligo and a second signaling oligo. Preferably, the first signaling oligo sequence is complementary to the second signaling oligo. Preferably, the first signaling oligo and the second signaling oligo can not form a stable association with each other through hydrogen bonding unless the first and second signaling oligos are brought into close proximity to each other through the mediation of a third party agent.

As used herein, the term "linker" or "linker molecule" refers to a polymer attached to an epitope binding agent construct. The attachment may be covalent or non-covalent. It is envisioned that the linker can be a polymer of amino acids or nucleotides. A preferred linker molecule is flexible and does not interfere with the binding of a nucleic acid binding factor to the set of nucleic acid components.

As used herein, the term "macromolecular complex" refers to a composition of matter comprising a macromolecule. Preferably, these are complexes of one or more macromolecules, such as polypeptides, lipids, carbohydrates, nucleic acids, natural or artificial polymers and the like, in association with each other. The association may involve covalent or non-covalent interactions between components of the macromolecular complex. Macromolecular complexes may be relatively simple, such as a ligand bound polypeptide, relatively complex, such as a lipid raft, or very complex, such as a cell surface, virus, bacteria, spore and the like. Macromolecular complexes may be biological or non-biological in nature.

As various changes could be made in the methods described herein without departing from the scope of the invention, it is intended that all matter contained in the above description and in the examples given below, shall be interpreted as illustrative and not in a limiting sense.

EXAMPLES

The following examples illustrate the invention.

Example 1

Methods for Selecting Aptamers for Use in Molecular Sensors

Figure 1:
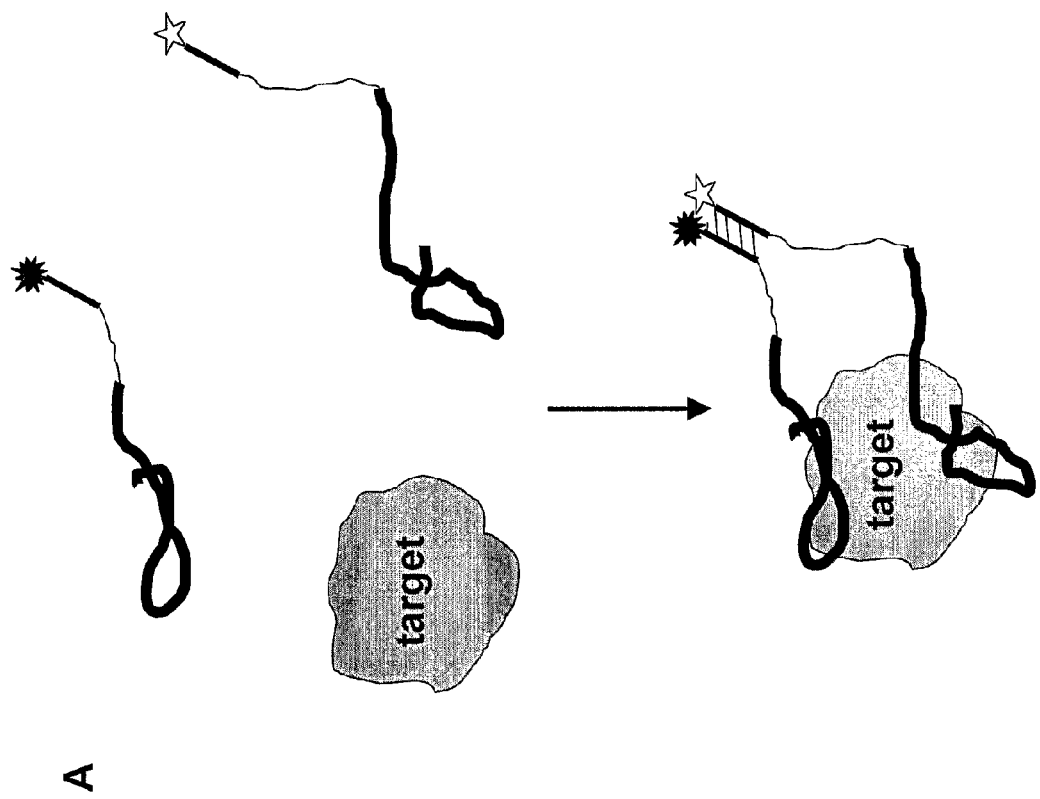
FIGS. 1A,B depicts a series of schematics illustrating molecular biosensors for detecting target molecules. (A) Variant of the design for target molecules lacking natural DNA binding activity. The biosensor in this case will be composed of two aptamers developed to recognize two different epitopes of the target molecule. (B) Variant of the design for a target molecule exhibiting natural DNA binding activity. The biosensor in this case will be composed of a short double-stranded DNA fragment containing the DNA sequence corresponding to the DNA-binding site and an aptamer developed to recognize a different epitope of the target molecule.
Figure 1:
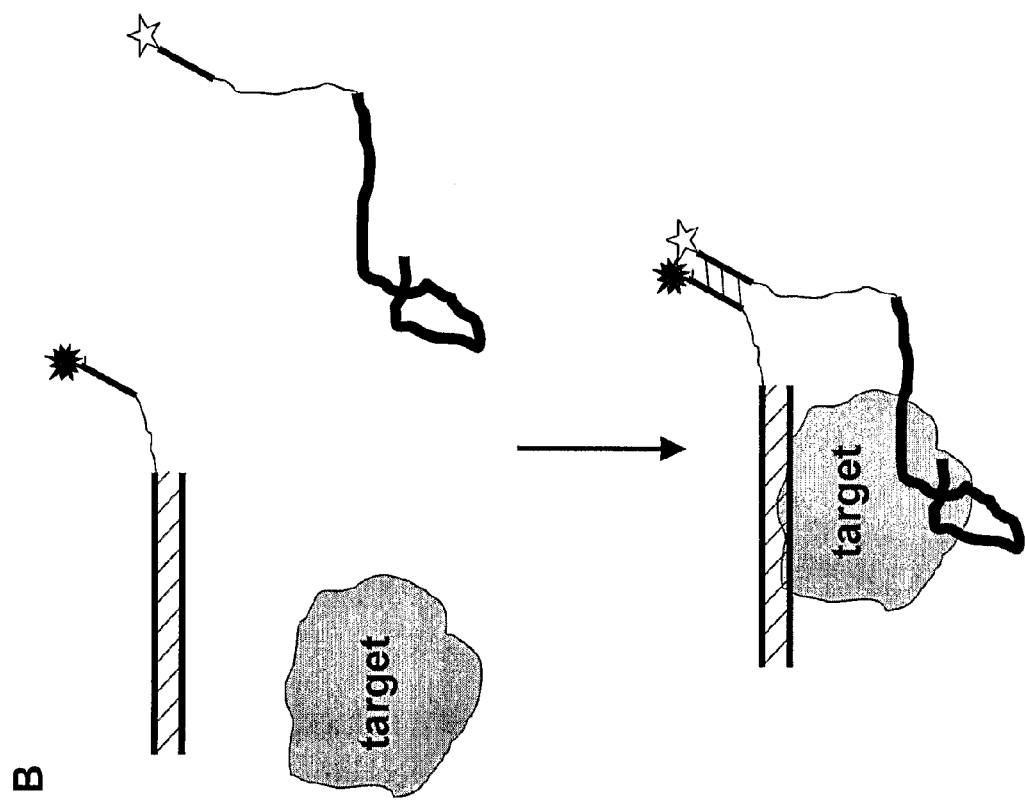
Figure 2:
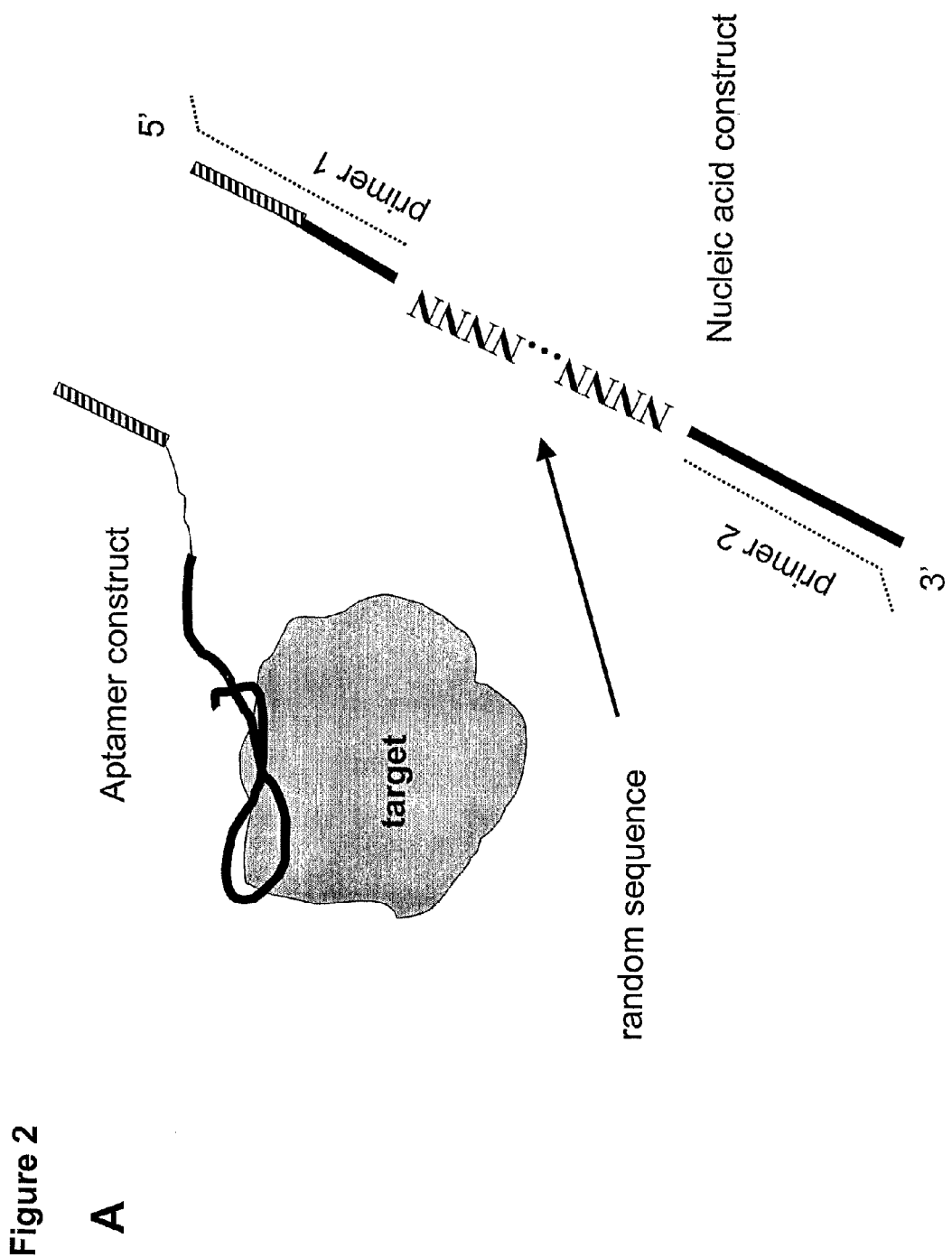
FIGS. 2A-E depicts a series of schematics illustrating methods for preparing aptamers according to the invention. (A) Selection of an aptamer in the presence of a known aptamer construct. The process is initiated with a nucleic acid construct, an aptamer construct (composed of an known aptamer (thick black line), a linker, and a short oligonucleotide sequence (hatched bar)), and the target molecule (grey). The hatched bars depict complementary short oligonucleotide sequences. (B) Simultaneous selection of two aptamers that bind distinct epitopes of the same target molecule (grey). The process is initiated with two types of nucleic acid constructs (the primer1-2 construct and the primer3-4 construct) and the target molecule. The hatched bars depict short complementary sequences at the end of the two types of nucleic acid constructs. (C) Alternative design for simultaneous selection of two aptamers that bind distinct epitopes of the same target molecule (grey). An additional pair of short oligonucleotides (hatched bars) connected by a flexible linker is present during the selection process. These oligonucleotides will be complementary to short oligonucleotide sequences at the end of the nucleic acid constructs (in primer 1 and primer 4). Their presence during selection will provide a bias towards selecting pairs of aptamers capable of simultaneously binding to the target molecule. Before cloning of the selected nucleic acid constructs the pairs of selected sequences will be ligated to preserve the information regarding the preferred pairs between various selected constructs. (D) Selection of an aptamer in the presence of a known antibody construct. The process is initiated with a nucleic acid construct, an antibody construct (composed of a known antibody (thick black line), a linker, and a short oligonucleotide sequence (hatched)), and the target molecule (grey). The hatched bars depict complementary short oligonucleotide sequences. (E) Selection of an aptamer in the presence of a known double-stranded DNA construct. The process is initiated with a nucleic acid construct, a double-stranded DNA construct (composed of an known double-stranded DNA sequence, a linker, and a short oligonucleotide sequence (hatched)), and the target molecule (grey). The hatched bars depict complementary short oligonucleotide sequences.
Figure 2:
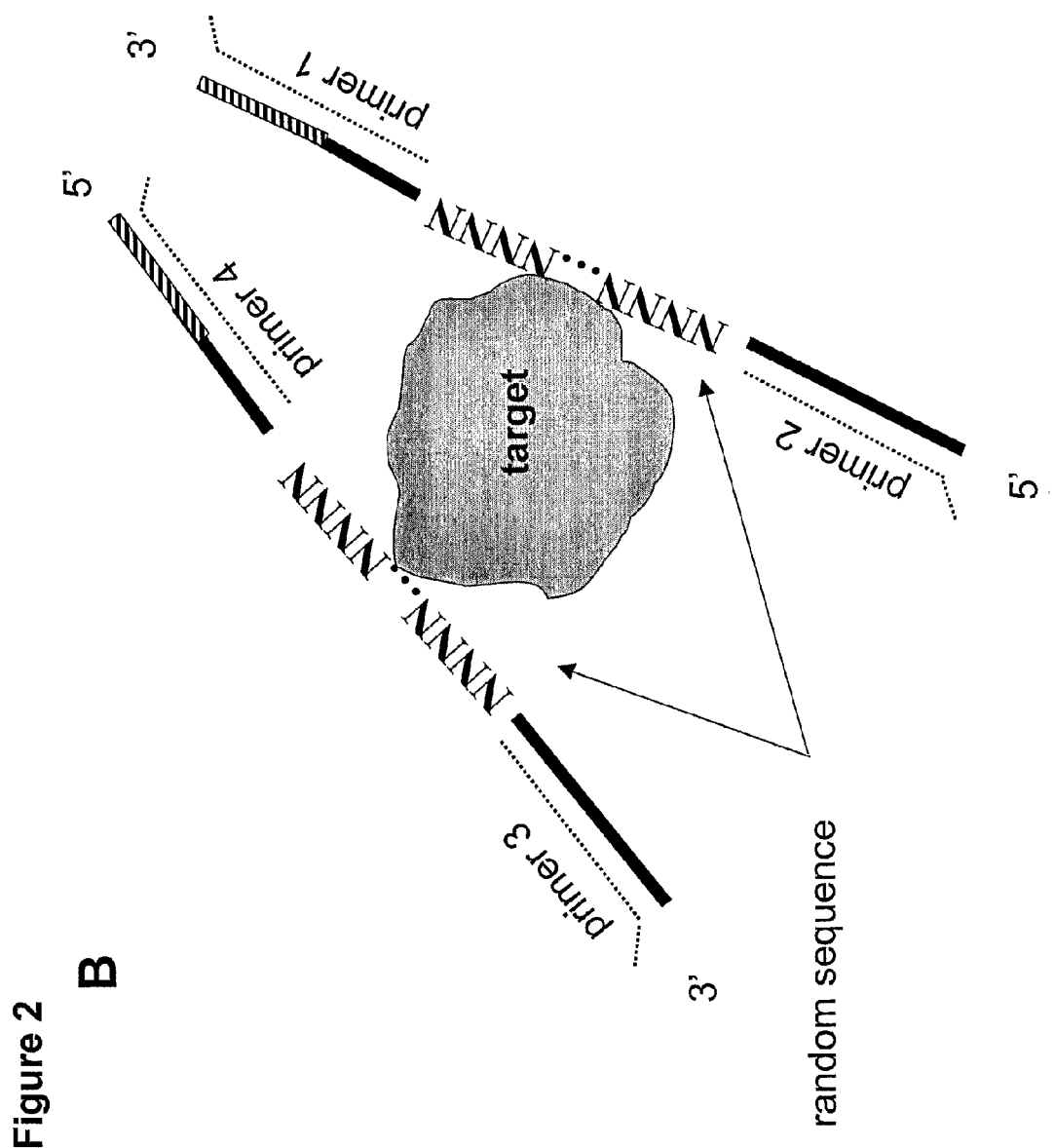
Figure 2:
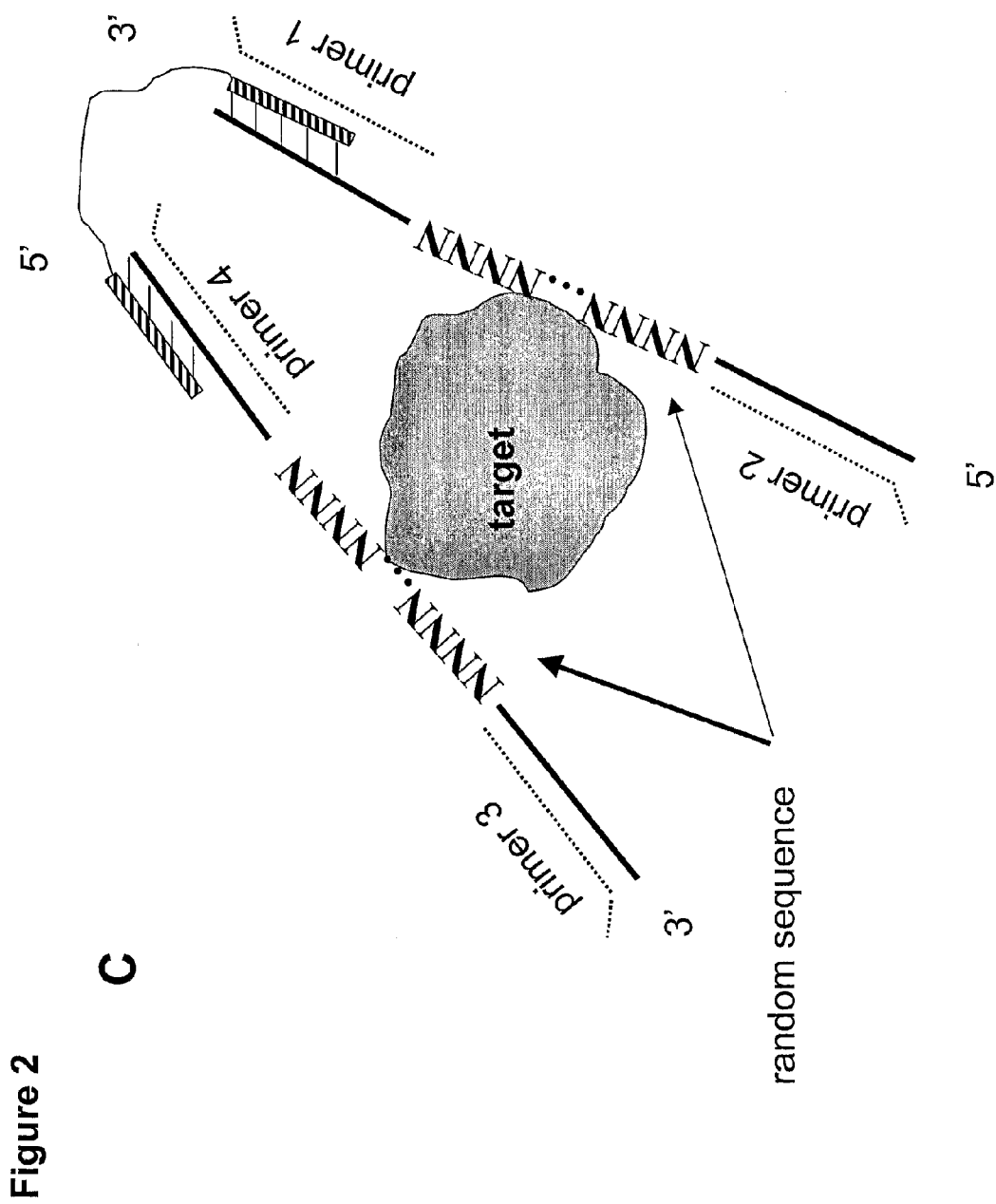
Figure 2:
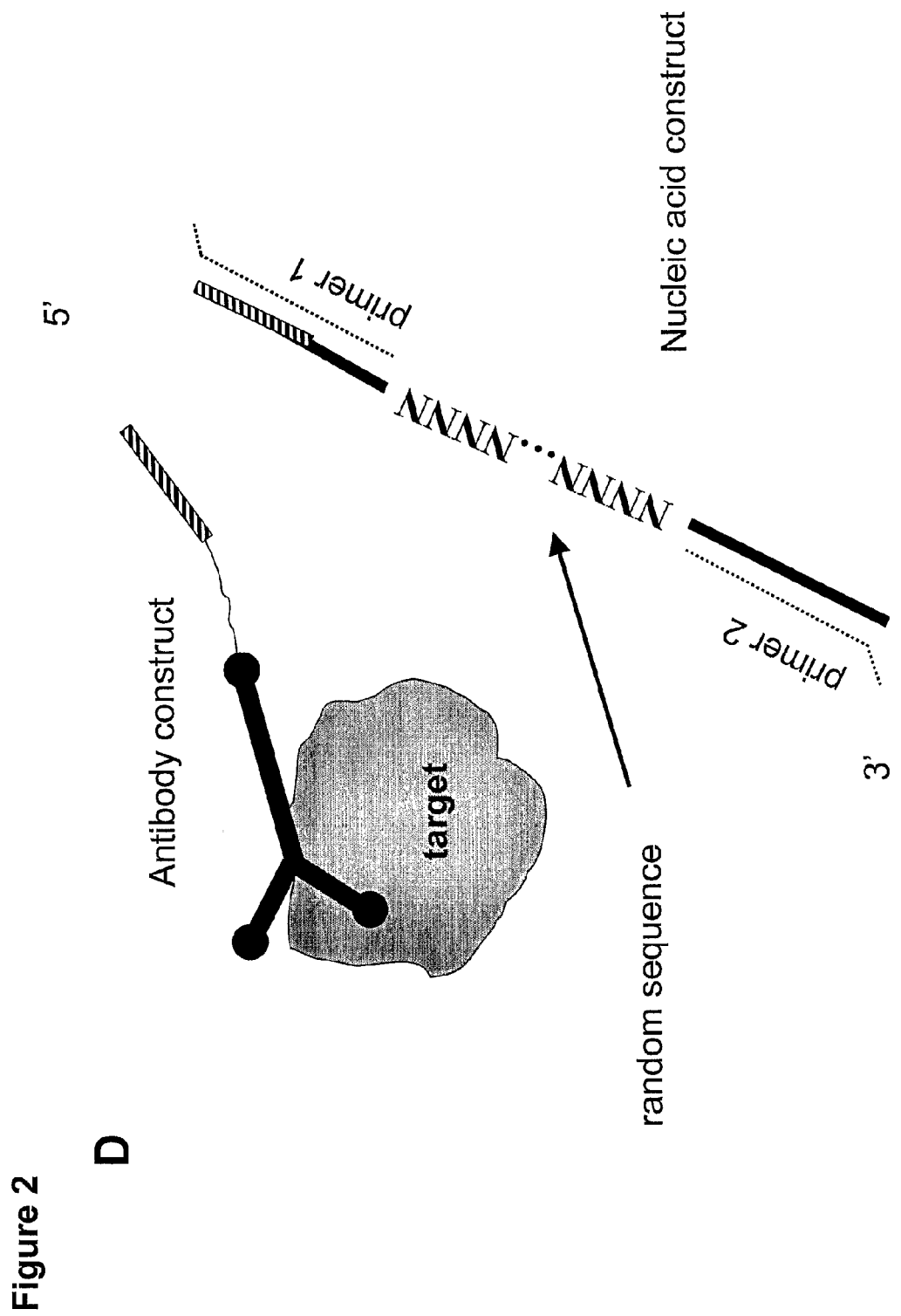
Figure 2:
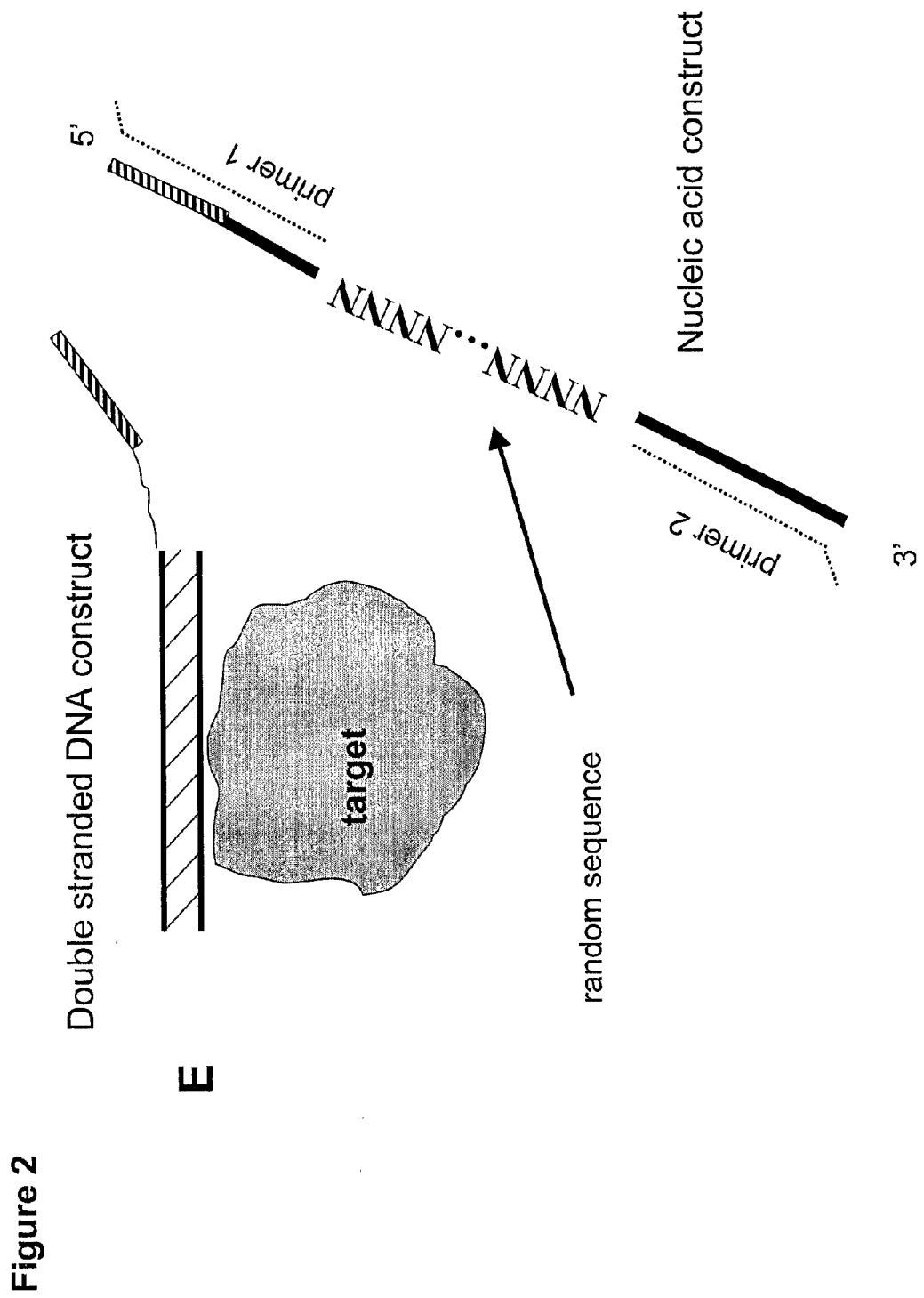

FIG. 2 summarizes five possible methods for selecting aptamers useful in the practice of the invention. Panel A depicts the selection of an additional aptamer in the presence of a target bound to a known aptamer. The nucleic acid construct is comprised of a signaling oligo, represented by the hatched bar, and two primers flanking a random DNA sequence. In practice, the signaling oligo is treated as a specific subpart of the primer in the nucleic acid construct. A complimentary signaling oligo is attached to the pre-selected aptamer via a long flexible linker. Here, the process begins by combining the nucleic acid construct, the target, and the known aptamer construct. Selection of aptamers using such a random sequence construct will be biased towards aptamers capable of binding to the target at an epitope distinct from the epitope of the known aptamer construct, and that will function in molecular biosensors depicted in FIG. 3A.

An alternative scenario is depicted in panel B, which describes the simultaneous selection of two aptamers binding two distinct epitopes of the target. The nucleic acid constructs are comprised of signaling oligos (represented by the hatched bars at the end of primer 1 and primer 4) and two primers flanking either side of a random-sequence. There are at least two different types of nucleic acid constructs, each type containing unique primer sequences. In panel B, one type contains primers 1 and 2, and the second contains primers 3 and 4. In this example, the process begins with combining both types of nucleic acid constructs, and the target. Selection of aptamers using such random sequence constructs will be biased towards aptamers capable of binding to the target simultaneously at two distinct epitopes of the protein, and that will function in sensors depicted in FIG. 3A.

Panel C depicts an alternative design for simultaneous selection of two aptamers binding two distinct epitopes of the target. In addition to the two different types of nucleic acid constructs, a third bridging construct is used. The bridging construct comprises an additional pair of short oligonucleotides (hatched bars) connected by a flexible linker. These oligonucleotides will be complementary to the short oligonucleotides at the end of the nucleic acid constructs. The presence of the bridging construct during selection will provide a bias towards selecting pairs of aptamers capable of simultaneously binding the target. Before cloning of the selected aptamers (after the last selection) the pairs of selected sequences will be enzymatically ligated using T4 ligase to preserve the information regarding the preferred pairs between various selected aptamers.

In a fourth alternate embodiment, a second aptamer can be selected in the presence of a target bound by an antibody (FIG. 2 D). The signaling oligo in the nucleic acid construct, depicted by the hatched bar, is complementary to the signaling oligo attached to the antibody via a long flexible linker. The process begins by combining the nucleic acid construct, the target, and the antibody construct. Selection of an aptamer using such a random sequence construct will be biased towards aptamers able to bind to the protein at an epitope distinct from the antibody epitope and will function in sensors depicted in FIG. 3C.

In a fifth alternate embodiment, a second aptamer can be selected in the presence of the target bound to a double-stranded DNA fragment (FIG. 2E). The signaling oligo in the nucleic acid construct, depicted by the hatched bar, is complementary to the signaling oligo attached to the double-stranded DNA construct via a long flexible linker. The process begins by combining the nucleic acid construct, the target, and the double-stranded DNA construct. Selection of an aptamer using such a random sequence construct will be biased towards aptamers able to bind to the target at a site distinct from the double-stranded DNA binding site and will function in sensors depicted in FIG. 3B.

Example 2

Figure 5:
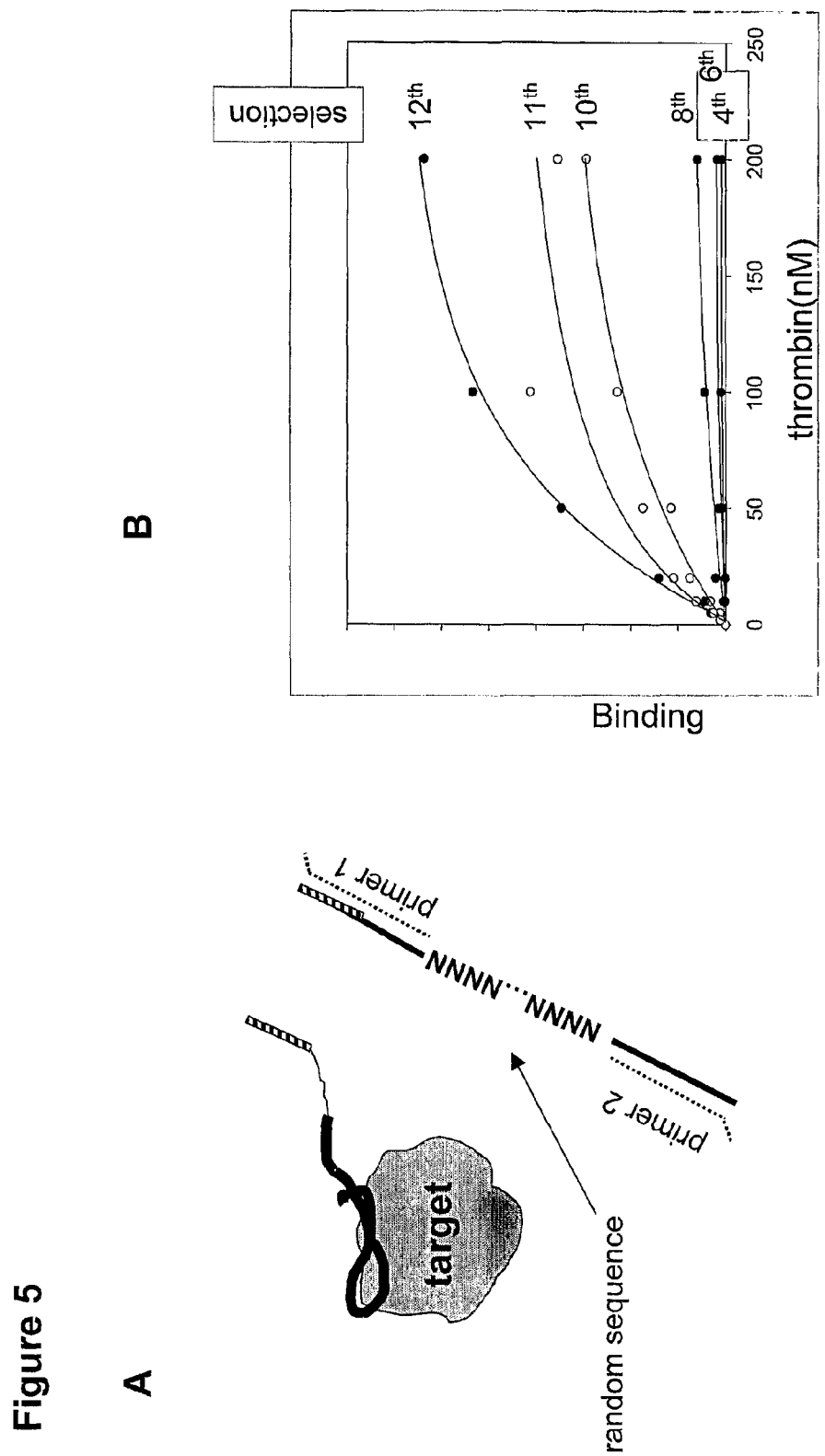
FIGS. 5A-C summarizes the selection of an aptamer that binds to thrombin at an epitope distinct from the binding site of the G15D aptamer. (A) An illustration of the reagents used to begin the process of selection. (B) The graph indicates the increase in thrombin binding with successive rounds of selection. (C) The sequences represent aptamers developed after 12 rounds of selection.

Sequential Selection of Aptamers that Bind to Thrombin for Use in Making a Thrombin Sensor The results of selecting an aptamer in the presence of a known aptamer construct are depicted in FIG. 5. The in vitro evolution procedure was initiated using a selection construct containing a 33 nt random sequence (THR11)(Table 1) in the presence of the known THR22 aptamer construct (THR22) (Table 1) and the target, in this case thrombin (FIG. 5A). Five µM of THR11 were added to 5 µM THR22 in a total of 1 mL of buffer (50 mM Tris-HCl (pH 7.5), 100 mM NaCl, 5 mM KCl and 1 mM $MgCl_2$). The mixture was boiled for approximately 1 min, and allowed to cool to room temperature (RT). Thrombin (200 nM) was added, and the mixture was incubated for 15-30 min at RT. Next, the mixture was spun through a nitrocellulose filter (NCF), followed by 2 washes of 1 mL and a single wash of 0.5 mL. Pre-warmed urea (200 µL of 7M solution containing 1M NaCl) was loaded on the NCF, and incubated for 15 min at 37° C. The DNA/urea mixture was eluted, and the DNA was precipitated with ethanol (added cold ethanol (2.5× the volume of eluted DNA) and incubated for at least two hours at −20° C.). The precipitated DNA was centrifuged, the supernatant removed, and the subsequent pellet was dried in a speed-vac. The pellet was re-dissolved in 20 µL of water, and used as a template for the PCR reaction.

Each PCR reaction contained 80 µL of dd H2O, 10 µL of 10×PCR buffer, 6 µL of $MgCl_2$, 0.8 µL 25 mM dNTPs, 1 µL 50 uM primer 1 (modified with fluorescein), 1 uL 50 µM primer 2 (biotinylated), 0.5 µL Taq polymerase, and 1 µL of template. The reaction cycle consisted of 5 min at 95° C., sixteen cycles of 30 s at 95° C., 30 s at 50° C., and 1 min at 72° C., and 5 min at 72° C. The pooled samples were allowed to cool, and subsequently separated on a polyacrylamide gel. The band(s) of interest were visualized by utilizing the fluorescein tag, and were excised from the gel. The gel pieces were transferred to a microtube and crushed using a pipet tip. The gel pieces were covered with diffusion buffer (100 mM Tris (pH 8.0), 0.5 M NaCl, 5 mM EDTA) and the mixture was incubated for at least two hours at 50° C. After centrifugation the supernatant was filtered through an empty Bio-Rad microspin column. The gel pieces were washed with fresh diffusion buffer, and the process repeated for a second time. The supernatants from the first and second procedures were combined.

Pre-equilabrated (1 M NaCl, 50 mM Tris (pH 8.0), and 1 mM EDTA) DYNAL magnetic streptavidin beads were mixed with the gel-purified DNA, and incubated at RT for 30 min with constant shaking. The supernatant was removed, and the beads were washed once with 500 µL, once with 250 µL, and once with 100 µL of buffer. Next, the beads were incubated for 30 min at 37° C. with 50 µL of 0.15N NaOH. The supernatant containing the fluorescein labeled DNA was removed and filtered through a G-25 Sephadex microspin column pre-equilibrated with buffer. The estimated concentration of the recovered DNA was calculated by comparison to a known amount of fluorescein-labeled primer.

The second round of selection began by combining 50 nM of the recovered DNA and 50-1000 nM of THR22 in a total of 50 µL of selection buffer. The DNA mixture was boiled for 1 min, and allowed to cool to RT. Subsequently, the DNA mixture was filtered through a pre-equilibrated NCF to remove DNA sequences with affinity for the NCF. Thrombin (20 nM) was added to the filtered DNA and the mixture was incubated for 15-10 min at RT. Next, the mixture was spun through another pre-equilibrated NCF, followed by two washes of 100 µL. After incubation with 100 µL of urea (7M in a buffer of 1M NaCl) for 15 min at 37° C., the DNA-thrombin complexes were eluted from the NCF. The DNA in the eluted solution was precipitated with alcohol (see above) and re-suspended in 20 µL of water. This was used as a template for the PCR reaction. PCR products were purified by electrophoresis on polyacrylamide gel and the single-stranded DNA was obtained from purified PCR products as described above for the first selection. Subsequent selections were repeated until the detected thrombin-binding activity reached a maximum (FIG. 5B).

Panel B depicts the thrombin-binding activity of single-stranded DNAs obtained after each indicated round of selection. Measurable thrombin-binding activity appeared after the 4th selection and reached maximum binding activity after the 12th selection. Binding was measured in the presence of excess THR22. DNA obtained after the 12th selection was cloned and the DNA from individual clones was sequenced. Panel C depicts the sequence alignment (using ClustalX) of the individual clones. Clones obtained from 4 independent selection experiments are shown. These selections were performed using the following pairs of aptamer constructs and selection constructs: THR22 and THR 11; THR25 and THR 11; THR42 and THR11; THR43 and THR 11 (Table 1). Several families of highly conserved sequences are easily visible in panel C.

Figure 6:
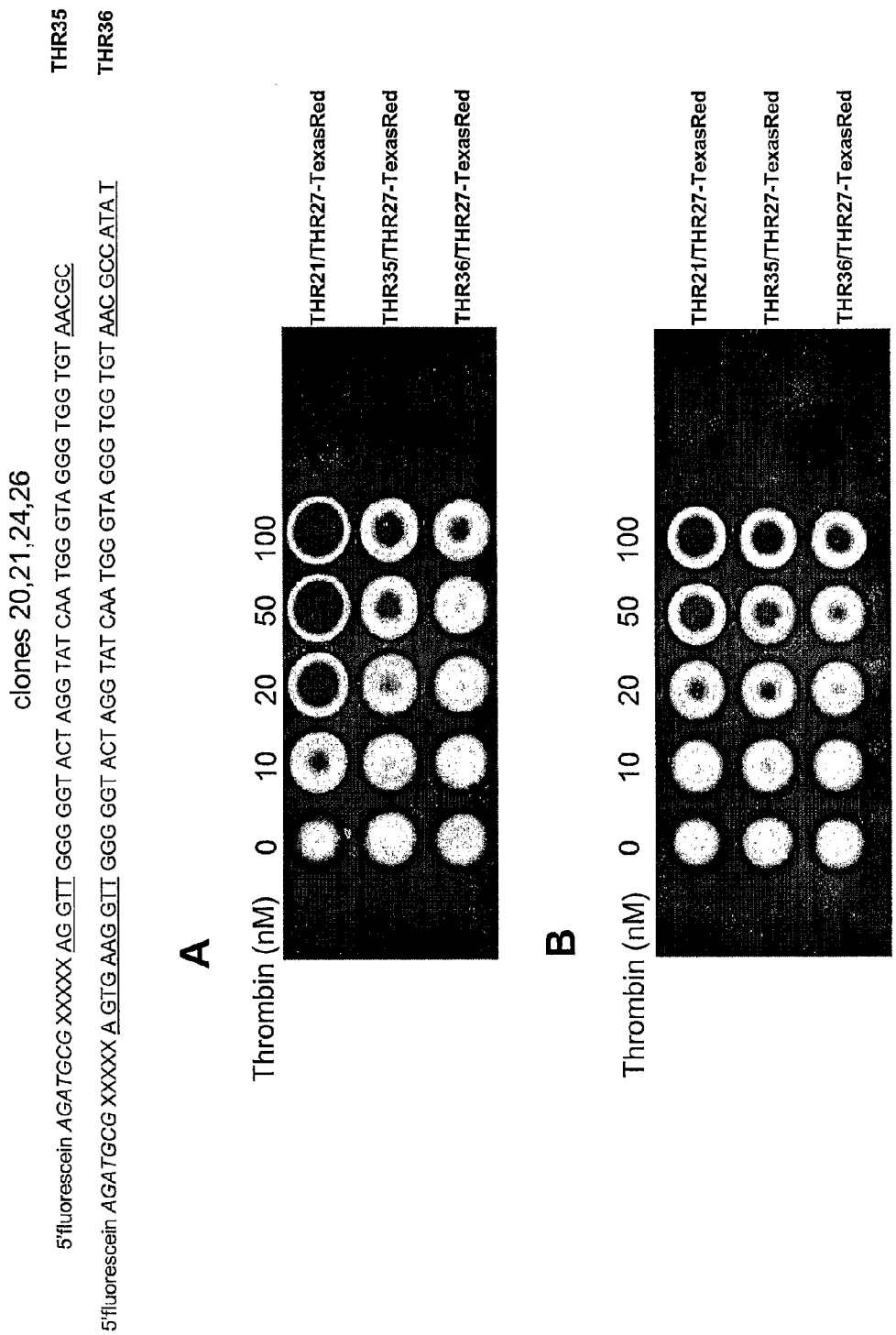
FIGS. 6A,B demonstrates the functional thrombin sensor comprising Texas Red-labeled THR27 and fluorescein-labeled THR35 or THR36 (both contain the sequence corresponding to that of clones 20, 21, 24, and 26 of FIG. 5C). The fluorescence image represents the specificity of either 20 nM (A) or 100 nM (B) of the indicated biosensor.

One sequence, which appeared in 4 clones (clones 20, 21, 24, and 26) shown in FIG. 5, was used to create a functional thrombin biosensor (FIG. 6). The cloned sequence was used in two separate aptamer constructs. Each construct (THR 35 and THR 36) was comprised of the aptamer sequence, a linker, and a fluorescein-labeled signaling oligo. As shown in FIG. 6, THR 35 and THR 36 differ in the nucleotides flanking the cloned sequence. The other half of the thrombin biosensor (THR27, Table 1) contained the same aptamer sequence as the THR22 aptamer construct used in the selection, a linker, and a Texas Red-labeled complementary signaling oligo. Panels A and B depict the fluorescence image (sensitized acceptor emission) of microtiterplate wells containing 20 nM (panel A) or 100 nM (panel B) of the indicated thrombin sensor and the indicated concentrations of thrombin. For comparison, a sensor comprising aptamer constructs containing previously described thrombin aptamers (THR21 and THR27, Table 1) is shown.

Example 3

Simultaneous Selection of Aptamers that Bind to Thrombin

Figure 7:
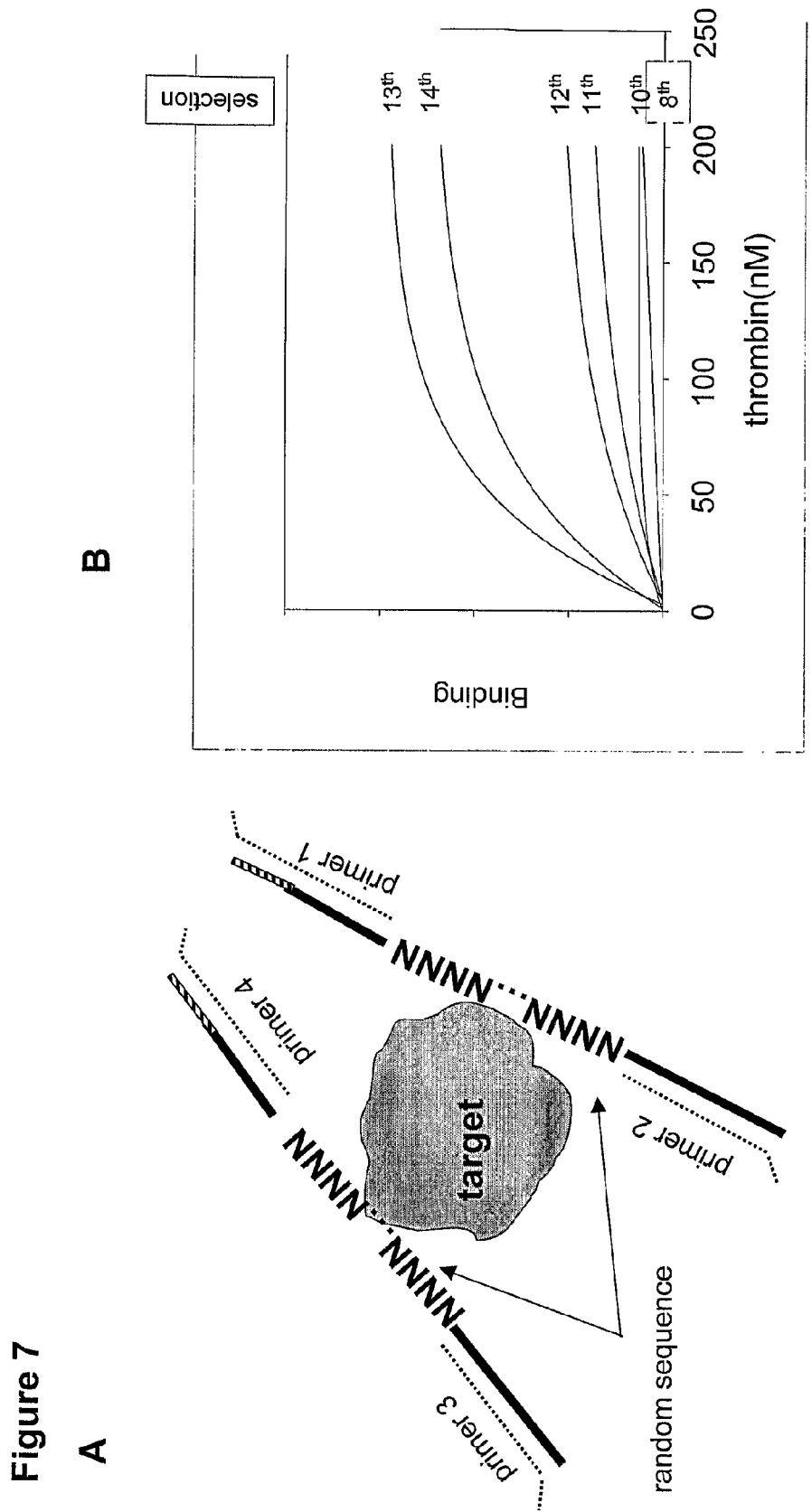
FIGS. 7A-C summarizes the simultaneous selection of two aptamers that bind to thrombin at distinct epitopes. (A) An illustration of the reagents used to begin the process of selection. (B) The graph indicates the increase in thrombin binding with successive rounds of selection. (C) The sequences represent aptamers developed after 13 rounds of selection.

FIG. 7 depicts the results of simultaneously selecting two aptamers that bind to a target at distinct epitopes. The selection procedure began with two types of selection constructs, each containing a 30 nt random sequence (THR49 and THR50) (Table 1), and the target thrombin (panel A). The process proceeds as outlined above, with the exception that two sets of PCR reactions were performed, corresponding to the two different types of nucleic acid constructs initially used. The thrombin-binding activity of the mixture of single-stranded DNAs obtained after each indicated round of selection is shown in panel B. Measurable thrombin-binding activity appeared after the 6th selection and reached a maximum after the 14th selection. DNA obtained after the 14th selection was cloned and the DNA from individual clones was sequenced. Panel C depicts the sequence alignment (using ClustalX) of the clones. Several families of highly conserved sequences are easily visible.

Example 4

Selection of an Aptamer for Use in a CRP Sensor with Double-strandedDNA

Figure 8:
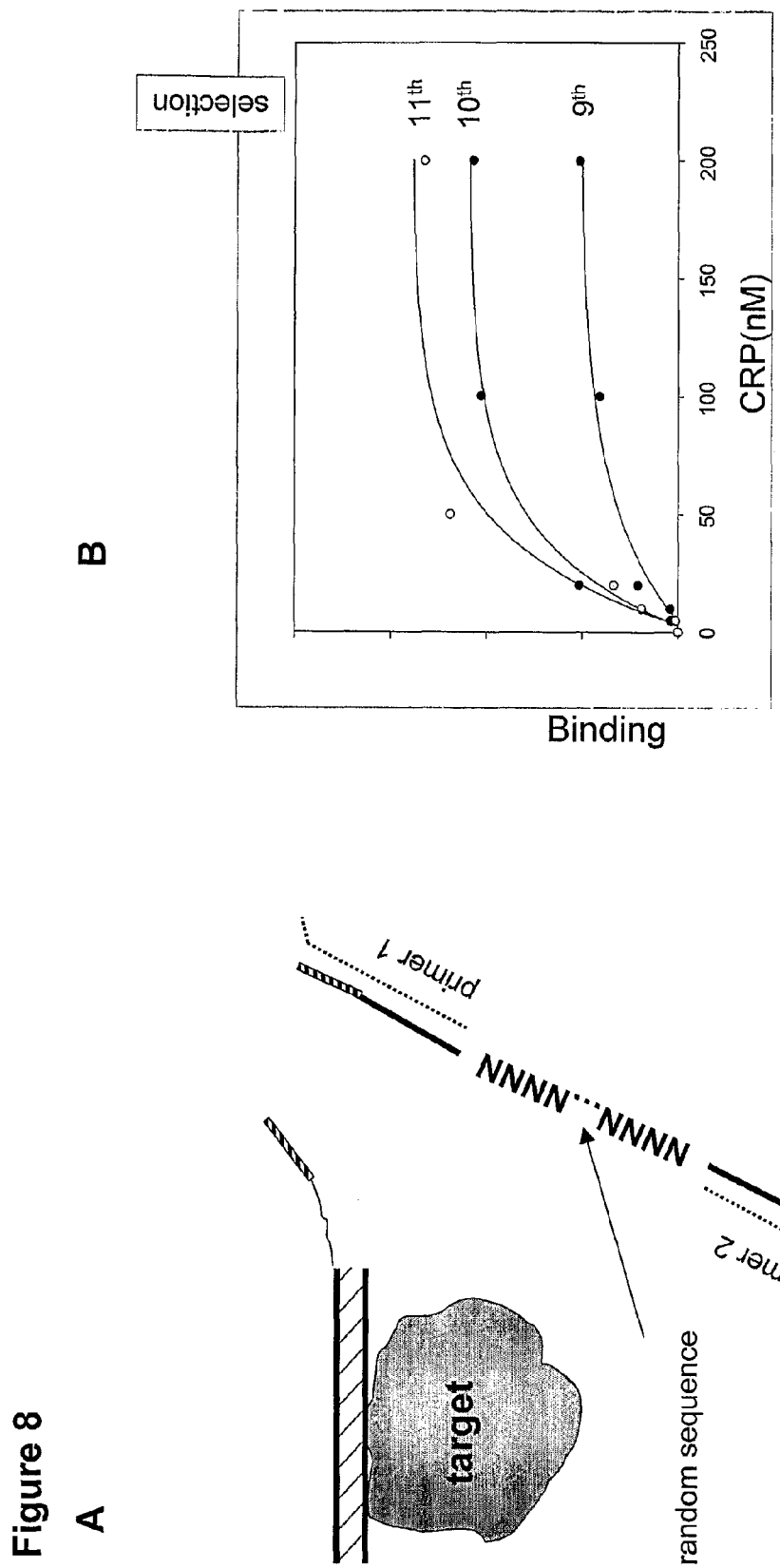
FIGS. 8A-C summarizes the selection of an aptamer that binds to CRP at an epitope distinct from the DNA-binding site. (A) An illustration of the reagents used to begin the process of selection. (B) The graph indicates the increase in thrombin binding with successive rounds of selection. (C) The sequences represent aptamers developed after 11 rounds of selection.

FIG. 8 depicts the selection of an aptamer in the presence of a double-stranded DNA molecular recognition construct. Aptamers to the cAMP binding protein ("CRP") were selected to bind at sites distinct from the DNA-binding site of the protein. Selection was initiated with a nucleic acid construct containing a 33 nt random sequence (MIS12) (Table 1). Additionally, a double-stranded DNA construct comprised of the CRP DNA binding site sequence (MIS10X3 hybridized with MIS11), a linker, and a signaling oligo was used for the process. (FIG. 8A). The selection process was essentially the same as outlined above for the thrombin aptamer. The only difference was that the buffer used in the selection contained 200 μL c-AMP, which is required for the double-stranded DNA construct to bind to CRP. In the first selection ~5 uM MIS12 was combined with 400 nM MIS10X3/MIS11, 400 nM CRP, and 0.2 mM c-AMP. In subsequent selections 100 nM MIS10X3/MIS11, 50 nM selected single-stranded DNA constructs and 100 nM CRP were combined.

CRP binding activity of single-stranded DNA obtained after the indicated round of selection is depicted in FIG. 8B. Measurable CRP binding activity appeared after the 6th selection and reached a maximum after the 12th selection. Binding was measured in the presence of excess MIS10X3/MIS11. DNA obtained after the 12th selection was cloned and the DNA obtained from individual clones was sequenced. The sequence alignment (using ClustalX) of the clones is depicted in panel C. A conserved core sequence of ~16 nucleotides could be identified.

TABLE 1

| Construct | Sequence | Sequence Identifier | Description |
|---|---|---|---|
| THR11 | CTG TCG TTA GTG AAG GTT NNN NNN NNN NNN NNN NNN NNN NNN NNN NNN NNN AAC GCC ATA TCA CAG ACG | SEQ ID NO: 1 | Construct containing 33 nt random DNA sequence for thrombin aptamer selection |
| THR22 | GGT TGG TGT GGT TGG (Spacer18)$_2$ GA CAG | SEQ ID NO: 2 | Co-aptamer for thrombin aptamer selection |
| THR25 | GGT TGG TGT GGT TGG (Spacer18)$_5$ AC GA CAG | SEQ ID NO: 3 | Co-aptamer for thrombin aptamer selection |
| THR42 | GGT TGG TGT GGT TGG (Spacer18)$_5$ AAC GAC AG | SEQ ID NO: 4 | co-aptamer for thrombin aptamer selection |
| THR43 | CTG TCG TT (Spacer18)$_5$ TTGAGTCAGCGTCGAGCA NNN NNN NNN NNN NNN NNN NNN NNN NNN NNN NNN TTC ACT GTG CTG CGG CTA | SEQ ID NO: 5 | Construct containing 33 nt random DNA sequence for thrombin aptamer selection |
| THR27 | GGT TGG TGT GGT TGG (Spacer18)$_5$ (C6 amino-dT) C GCA TCT | SEQ ID NO: 6 | G15D aptamer connected via 5 Spacer18 linkers to 7 nt "signaling" oligonucleotide containing amino-dT (near its 5' end) |
| THR35 | 5' fluorescein AGA TGC G (Spacer18)$_5$ AG GTT GGG GGT ACT AGG TAT CAA TGG GTA GGG TGG TGT AAC GC | SEQ ID NO: 7 | Thrombin sensor component |
| THR36 | 5' fluorescein AGA TGC G (Spacer18)$_5$ A GTG AAG GTT GGG GGT ACT AGG TAT CAA TGG GTA GGG TGG TGT AAC GCC_ATA T | SEQ ID NO: 8 | Thrombin sensor component |
| THR21 | 5' fluorescein AGA TGC G (Spacer18)$_5$ AGT CCG TGG TAG GGC AGG TTG GGG TGA CT | SEQ ID NO: 9 | 7 nt "signaling" oligonucleotide labeled at 5' with fluorescein connected to 60-18 [29] aptamer via 5 Spacer18 linkers |
| THR49 | CACCTGATCGCTCCTCGT NNN NNN NNN NNN NNN NNN NNN NNN NNN NNN CAG GAT GCA CAG GCA CAA | SEQ ID NO: 10 | Construct containing 30 nt random DNA sequence for simultaneous selection of two thrombin aptamers |

TABLE 1-continued

| Construct | Sequence | Sequence Identifier | Description |
|---|---|---|---|
| THR50 | AGCCGCCATTCCATAGTG NNN NNN NNN NNN NNN NNN NNN NNN NNN NNN CAG GAT GCC GAT CAG GTG | SEQ ID NO: 11 | Construct containing 30 nt random DNA sequence for simultaneous selection of two thrombin aptamers |
| MIS12 | AGCCA T CTA ACT ATT CCC NNN NNN NNN NNN NNN NNN NNN NNN NNN NNN GAG CGA GAA ATT CTA GGT | SEQ ID NO: 12 | Construct containing 33 nt random DNA sequence for CRP aptamer selection |
| MIS10X3 | AAC GCA ATA AAT GTG AAG TAG ATC ACA TTT TAG GCA CC (Spacer18)$_5$ GA TGGCT | SEQ ID NO: 13 | co-aptamer for CRP aptamer selection |
| MIS11 | GGT GCC TAA AAT GTG ATC TAC TTC ACA TTT ATT GCG TT | SEQ ID NO: 14 | Complement to MIS10X3 |
| Clone 1 | GGCGGTATGG GCATAGCGTA ATGGGAGGTT GGT | SEQ ID NO: 15 | Clone from Figure 5 |
| Clone 2 | GGATGCGTAA TGGTTAGGGT GGGTAGGGTA TCC | SEQ ID NO: 16 | Clone from Figure 5 |
| Clone 3 | GGATGCGTAA TGGTTAGGGT GGGTAGGGTA TCC | SEQ ID NO: 17 | Clone from Figure 5 |
| Clone 4 | GGATGCGTAA TGGTTAGGGT GGGTAGGGTA TCC | SEQ ID NO: 18 | Clone from Figure 5 |
| Clone 5 | GCAGTAGGTA CTATATTGGC TAGGGTGGTC TGC | SEQ ID NO: 19 | Clone from Figure 5 |
| Clone 6 | GCAGTAGGTA CTATATTGGC TAGGGTGGTC TGC | SEQ ID NO: 20 | Clone from Figure 5 |
| Clone 7 | GGCGGTATGG GCATAGCGTA ATGGGAGGTC TGC | SEQ ID NO: 21 | Clone from Figure 5 |
| Clone 8 | GGATGCGTAA TGGTTAGGGT GGGTAGGGTA TCC | SEQ ID NO: 22 | Clone from Figure 5 |
| Clone 9 | GGCGGTATGG GTATAGCGTA ATGGGAGGTT GGT | SEQ ID NO: 23 | Clone from Figure 5 |
| Clone 10 | GGGGGTACTA GGTATTAATG GGTAGGGTGG TGT | SEQ ID NO: 24 | Clone from Figure 5 |
| Clone 11 | CAGCAGGGAA CGGAACGGTT AGGGTGGGTA GGG | SEQ ID NO: 25 | Clone from Figure 5 |
| Clone 12 | GCGGNGATAG GTCGCGTAAG TTGGGTAGGG TGG | SEQ ID NO: 26 | Clone from Figure 5 |
| Clone 13 | CAGGATGGGT AGGGTGGTCA GCGAAGCAGT AGG | SEQ ID NO: 27 | Clone from Figure 5 |
| Clone 14 | CAACGGTTGG GTGAACTGTA GTGGCTTGGG GTG | SEQ ID NO: 28 | Clone from Figure 5 |

TABLE 1-continued

| Construct | Sequence | Sequence Identifier | Description |
|---|---|---|---|
| Clone 15 | CAGGATGGGT AGGGTGGTCA GCGAAGCAGT AGG | SEQ ID NO: 29 | Clone from Figure 5 |
| Clone 16 | CAGGATGGGT AGGGTGGTCA GCGAAGCAGT AG | SEQ ID NO: 30 | Clone from Figure 5 |
| Clone 17 | GGCGAGAGCA GCGTGATAGG GTGGGTAGGG TGG | SEQ ID NO: 31 | Clone from Figure 5 |
| Clone 18 | CAGGGTCAGG GCTAGATGAT GCGATTAACC ATG | SEQ ID NO: 32 | Clone from Figure 5 |
| Clone 19 | CAGGATGGGT AGGGTGGTCA GCGAAGCAGT AGG | SEQ ID NO: 33 | Clone from Figure 5 |
| Clone 20 | GGGGGTACTA GGTATCAATG GGTAGGGTGG TGT | SEQ ID NO: 34 | Clone from Figure 5 |
| Clone 21 | GGGGGTACTA GGTATCAATG GGTAGGGTGG TGT | SEQ ID NO: 35 | Clone from Figure 5 |
| Clone 22 | GGAGACGTAA TGGGTTGGTT GGGAAGNGGA TCC | SEQ ID NO: 36 | Clone from Figure 5 |
| Clone 23 | GCATACGTAA TGGTCCGGTT GGGGCGGGTA TGT | SEQ ID NO: 37 | Clone from Figure 5 |
| Clone 24 | GGGGGTACTA GGTATCAATG GGTAGGGTGG TGT | SEQ ID NO: 38 | Clone from Figure 5 |
| Clone 25 | GAGGGGACTT AGGATGGGTA GGGTGGTAGG CCC | SEQ ID NO: 39 | Clone from Figure 5 |
| Clone 26 | GGGGGTACTA GGTATCAATG GGTAGGGTGG TGT | SEQ ID NO: 40 | Clone from Figure 5 |
| Clone 27 | GGTCGGGGCA TAGTAATGCT GGATTGGGCA GCT | SEQ ID NO: 41 | Clone from Figure 5 |
| Clone 28 | GGGTAGGAGC AGTACACGCT GGAATGGGTC ACT | SEQ ID NO: 42 | Clone from Figure 5 |
| Clone 29 | GCAGTAGGTA CTATATTGGC TAGGGTGGTC TGC | SEQ ID NO: 43 | Clone from Figure 5 |
| Clone 30 | GGGTAGGGTG ACAGGGAGGA CGGAATGGGC ACT | SEQ ID NO: 44 | Clone from Figure 5 |
| Clone 31 | GCAGTAGGTA CTATATTGGC TAGGGTGGTC TGC | SEQ ID NO: 45 | Clone from Figure 5 |
| Clone 32 | GCAGTAGGTA CTATATTGGC TAGGGTGGTC TGC | SEQ ID NO: 46 | Clone from Figure 5 |
| Clone 33 | GCAGTAGGTA CTATATTGGC TAGGGTGGTC TGC | SEQ ID NO: 47 | Clone from Figure 5 |

TABLE 1-continued

| Construct | Sequence | Sequence Identifier | Description |
|---|---|---|---|
| Clone 34 | GGGGGTGCTA GGTATTAAAG GGTAGGGTGG TGT | SEQ ID NO: 48 | Clone from Figure 5 |
| Clone 35 | GCAGTAGGTA CTATGTCGGG TCGGGTGGTC TGC | SEQ ID NO: 49 | Clone from Figure 5 |
| Clone 1-1 | GGGTAGGGTG GTTGTAATAG GGATTGCGAT | SEQ ID NO: 50 | Clone from Figure 7 |
| Clone 1-2 | GGGTAGGGTG GTTGTAATAG GGATTGCGAT | SEQ ID NO: 51 | Clone from Figure 7 |
| Clone 1-3 | GGCACAACCC GATATGGCTA TGAATCTGCC | SEQ ID NO: 52 | Clone from Figure 7 |
| Clone 1-4 | GGGTAGGGTG GTTGTAATAG GGATTGCGAT | SEQ ID NO: 53 | Clone from Figure 7 |
| Clone 1-5 | GGGTAGGGTG GTTGTAATAG GGATTGCGAT | SEQ ID NO: 54 | Clone from Figure 7 |
| Clone 1-6 | GGTGTGGGTG GTTATTGGTG TAGAGCGGGT | SEQ ID NO: 55 | Clone from Figure 7 |
| Clone 1-7 | AATGGGGAGG TTGGGGTGCG GGAGAGTGGT | SEQ ID NO: 56 | Clone from Figure 7 |
| Clone 1-8 | ACGCGTAGGA TGGGTAGGGT GGTCGCGTTA | SEQ ID NO: 57 | Clone from Figure 7 |
| Clone 1-9 | GGGTAGGGTG GTTGTAATAG GGATTGCGAT | SEQ ID NO: 58 | Clone from Figure 7 |
| Clone 1-10 | GGGCGAAGGT ACGAAGACGG ATGCACGTGC | SEQ ID NO: 59 | Clone from Figure 7 |
| Clone 2-1 | AAGGCCGCCA TCTGGGTCCG ACGAGTACCA | SEQ ID NO: 60 | Clone from Figure 7 |
| Clone 2-2 | TAGGGTGGGT AGGGTGGTCA ACTATGGGGG | SEQ ID NO: 61 | Clone from Figure 7 |
| Clone 2-3 | GGGTGGCTGG TCAAGGAGAT AGTACGATGC | SEQ ID NO: 62 | Clone from Figure 7 |
| Clone 2-4 | GGTAGGGTGG TTAAAATAGG GGAATGGCAG | SEQ ID NO: 63 | Clone from Figure 7 |
| Clone 2-5 | CACAAGAAGG GCGAGCGCTG AGCATAGTGC | SEQ ID NO: 64 | Clone from Figure 7 |
| Clone 2-6 | CCAACGACAC ATAGGGTACA CGCCGCCTCC | SEQ ID NO: 65 | Clone from Figure 7 |
| Clone 2-7 | GGTAGGGTGG TTAAAATAGG GGAATGGCAG | SEQ ID NO: 66 | Clone from Figure 7 |

TABLE 1-continued

| Construct | Sequence | Sequence Identifier | Description |
|---|---|---|---|
| Clone 2-8 | TAGGATGGGT AGGGTGGTCC CAGGAATGGC | SEQ ID NO: 67 | Clone from Figure 7 |
| Clone 2-9 | TAGGATGGGT AGGGTGGCCC CAGGAATGGC | SEQ ID NO: 68 | Clone from Figure 7 |
| Clone 2-10 | GGTAGGGTGG TTAAAATAGG GGAATGGCAG | SEQ ID NO: 69 | Clone from Figure 7 |
| Clone 2-11 | GATGTGGCCC AGAAGCATAA CACGACGTAC | SEQ ID NO: 70 | Clone from Figure 7 |
| Clone 2-12 | TAGGATGGGT AGGGTGGTCC CAGGAATGGC | SEQ ID NO: 71 | Clone from Figure 7 |
| Clone 2-13 | GGAGATGCAG GTACTGAGTA GGGAGTGTGC | SEQ ID NO: 72 | Clone from Figure 7 |
| Clone 2-14 | TAGGATGGGT AGGGTGGTCC CAGGAATGGC | SEQ ID NO: 73 | Clone from Figure 7 |
| Clone 1 | AATCAAGGGC TGGTGTTAAA GGTGATCGAC TAG | SEQ ID NO: 74 | Clone from Figure 8 |
| Clone 2 | AAGGGGAGCC ATCACACAGG AGGTCGCTTC GCT | SEQ ID NO: 75 | Clone from Figure 8 |
| Clone 3 | AAAGGCATCA CCTAGAGTTG CCGCCGATAC TTG | SEQ ID NO: 76 | Clone from Figure 8 |
| Clone 4 | GGGGATGTGC GAAACTGGTG ACTATGCGGG TGC | SEQ ID NO: 77 | Clone from Figure 8 |
| Clone 5 | CGAAAGGAGC CATCAACCTT GAAACGCCCG TCC | SEQ ID NO: 78 | Clone from Figure 8 |
| Clone 6 | CAGACGGGAG CCATCGACAT AGAGGTGATT GCC | SEQ ID NO: 79 | Clone from Figure 8 |
| Clone 7 | AGGGAAAGCC ATCACCTAGA CACATACAGC ATG | SEQ ID NO: 80 | Clone from Figure 8 |
| Clone 8 | ATAAGAAGCC ATCATAGGGA CCTAGCTAGC CCC | SEQ ID NO: 81 | Clone from Figure 8 |
| Clone 9 | CCAACAGACG GTAGCACAAC ACTAGTACTC TGG | SEQ ID NO: 82 | Clone from Figure 8 |
| Clone 10 | ACAGACGCCC CTAGTAAACA ATAACCGATG GCC | SEQ ID NO: 83 | Clone from Figure 8 |
| Clone 11 | ATAGCTACTC GCCAAGGGTG ACTTCTGCTA TTG | SEQ ID NO: 84 | Clone from Figure 8 |

TABLE 1-continued

| Construct | Sequence | Sequence Identifier | Description |
|---|---|---|---|
| Clone 12 | ATGGGGCAAC GCGGAGACCT GTCGGTACTG CCT | SEQ ID NO: 85 | Clone from Figure 8 |
| Clone 13 | GCAATATAGC ACTAAGCCTT AACTCCATGG TGG | SEQ ID NO: 86 | Clone from Figure 8 |
| Clone 14 | GCAAGGAAAA ACAAGCAAGC CATCACGACC TAG | SEQ ID NO: 87 | Clone from Figure 8 |
| Clone 15 | CAGGCATCCC AAGAAGTGTC AGCCGTTTCG TGG | SEQ ID NO: 88 | Clone from Figure 8 |
| Clone 16 | CAACAGGAGA GCCCGACACA CAGATCTGGC CCC | SEQ ID NO: 89 | Clone from Figure 8 |
| Clone 17 | ACAAGCCATC ACGTGAATGC CGACCGGTAC TGT | SEQ ID NO: 90 | Clone from Figure 8 |
| Clone 18 | ACCGACAAAC AAGTCAATAC GGGACACGAT CCT | SEQ ID NO: 91 | Clone from Figure 8 |
| Clone 19 | CAGTGGGTCG GGTCACAGCC ATGAGTGTTG CTG | SEQ ID NO: 92 | Clone from Figure 8 |
| Clone 20 | AACGGGAAAG CCATCACCAT ATTTATCGTC CTG | SEQ ID NO: 93 | Clone from Figure 8 |
| Clone 21 | ACGGGCGCAA ACAAGATGTA CAAAAGCATG GTG | SEQ ID NO: 94 | Clone from Figure 8 |
| Clone 22 | AGCGGGATAG GGAACTATCG GACAATCGTC GTG | SEQ ID NO: 95 | Clone from Figure 8 |
| Clone 23 | GAGGATAAAA GCCATCAACT AGAATGCGCA TGG | SEQ ID NO: 96 | Clone from Figure 8 |

What is claimed is:

1. A method for selecting at least one aptamer in the presence of an epitope binding agent construct, wherein the aptamer sequence binds to a first epitope on a target molecule and the epitope binding agent construct binds to a second epitope on the target molecule; the method comprising:
   (a) contacting a plurality of nucleic acid constructs and the epitope binding agent construct with the target molecule to form a mixture of nucleic acid constructs, epitope binding agent constructs, and target molecules, the nucleic acid construct comprising:
      i) A-B-C-D;
   the epitope binding agent construct comprising:
      ii) P-Q-R;
   wherein:
   A and C are each different DNA sequences from about 10 to about 30 nucleotides in length, A and C together comprising a sequence to prime a polymerase chain reaction for amplifying the aptamer sequence;
   B is a single-stranded random nucleotide sequence from about 20 to about 110 nucleotides in length that contains specific sequences binding to a first epitope of the target molecule;
   D and R are a pair of complementary nucleotide sequences from about 2 to about 20 nucleotides in length, wherein D and R have a free energy for association from about 5.5 kcal/mole to about 8.0 kcal/mole at a temperature from approximately 21° C. to about 40° C. and at a salt concentration of approximately 1 mM to about 100 mM;
   P is an epitope binding agent selected from the group comprising an aptamer, an antibody, an antibody fragment, a double-stranded DNA sequence, a ligand, a ligand fragment, a receptor, a receptor fragment, a polypeptide, a peptide, a coenzyme, a coregulator, an allosteric molecule, and an ion;
   Q is a flexible linker; and
   (b) isolating from the mixture a complex comprising the target molecule having the nucleic acid construct bound to the first epitope and the epitope binding agent construct bound to the second epitope; and
   (c) purifying the nucleic acid construct from the complex.

2. The method of claim 1, wherein the epitope binding agent is an antibody selected from the group comprising polyclonal antibodies, ascites, Fab fragments, Fab' fragments, monoclonal antibodies, and humanized antibodies.

3. The method of claim 1, wherein the epitope binding agent comprises a monoclonal antibody.

4. The epitope binding agent constructs of claim 1, wherein Q is from 0 to about 500 angstroms in length.

5. The epitope binding agent constructs of claim 1, wherein Q is from about 50 to about 250 angstroms in length.

6. The epitope binding agent constructs of claim 1, wherein Q is comprised of a polymer of bifunctional chemical linkers.

7. The epitope binding agent constructs of claim 1, wherein Q is comprised of poly ethylene glycol Spacer 18.

* * * * *